US009670447B2

(12) United States Patent
Das et al.

(10) Patent No.: US 9,670,447 B2
(45) Date of Patent: Jun. 6, 2017

(54) MICROFABRICATED POLYMERIC VESSEL MIMETICS

(71) Applicant: The United States of America, as represented by the Secretary, Department of Health and Human Services, Washington, DC (US)

(72) Inventors: Chandan Das, Little Rock, AR (US); Ashley A. Jaeger, North Bethesda, MD (US); Thomas J. Pohida, Monrovia, MD (US); Michael M. Gottesman, Bethesda, MD (US); Randall H. Pursley, Gaithersburg, MD (US); Philip G. McQueen, Silver Spring, MD (US); Nicole Y. Morgan, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 30 days.

(21) Appl. No.: 14/166,744

(22) Filed: Jan. 28, 2014

(65) Prior Publication Data
US 2014/0212967 A1    Jul. 31, 2014

Related U.S. Application Data

(60) Provisional application No. 61/758,198, filed on Jan. 29, 2013, provisional application No. 61/773,064, filed on Mar. 5, 2013.

(51) Int. Cl.
*A01N 1/02* (2006.01)
*C12M 1/12* (2006.01)
(Continued)

(52) U.S. Cl.
CPC .......... *C12M 25/02* (2013.01); *B29D 99/005* (2013.01); *C12N 5/0068* (2013.01); *C12N 2533/30* (2013.01)

(58) Field of Classification Search
CPC .................................................. C12N 5/0693
See application file for complete search history.

(56) References Cited

U.S. PATENT DOCUMENTS 5,002,572 A * 3/1991 Picha ...................... A61F 2/022
424/424
5,244,799 A    9/1993 Anderson
(Continued)

FOREIGN PATENT DOCUMENTS

WO    WO2012/003370    1/2012

OTHER PUBLICATIONS

Deok-Ho Kim, et al., *Guided Three-Dimensional Growth of Functional Cardiomyocytes on Polyethylene Glycol Nanostructures*, American Chemical Society, 2006.
(Continued)

*Primary Examiner* — Thomas J Sweet
*Assistant Examiner* — Wade P Schutte
(74) *Attorney, Agent, or Firm* — Klarquist Sparkman, LLP

(57) ABSTRACT

The present disclosure is directed to embodiments of microstructured membranes, methods of fabricating microstructured membranes, bioreactors housing microstructured membranes, and methods of using bioreactors and microstructured membranes. In some embodiments, the present disclosure allows culturing of cellular tissues in an environment which more accurately resembles a native environment. In some more specific embodiments, the present
(Continued)

disclosure allows culturing of tumor cells on a membrane having a microfabricated pattern which mimics a native vasculature system.

33 Claims, 17 Drawing Sheets

(51) Int. Cl.
B29D 99/00 (2010.01)
C12N 5/00 (2006.01)

(56) References Cited

U.S. PATENT DOCUMENTS

| | | | |
|---|---|---|---|
| 5,470,739 | A | 11/1995 | Akaike et al. |
| 5,807,944 | A * | 9/1998 | Hirt ............. C08F 290/02 351/159.04 |
| 6,372,495 | B1 * | 4/2002 | Flendrig ......... A61M 1/3472 435/177 |
| 7,780,897 | B2 | 8/2010 | Wicker et al. |
| 2005/0214935 | A1 * | 9/2005 | Kuwabara .......... C12M 21/08 435/299.1 |
| 2010/0273667 | A1 | 10/2010 | Kotov et al. |
| 2010/0297233 | A1 | 11/2010 | Moretti et al. |
| 2011/0008443 | A1 | 1/2011 | Alsberg et al. |
| 2011/0306581 | A1 | 12/2011 | Rapoport et al. |
| 2012/0225814 | A1 | 9/2012 | Hanjaya-Putra et al. |
| 2013/0317133 | A1 * | 11/2013 | Scales ................ G02B 1/043 523/107 |
| 2014/0093962 | A1 * | 4/2014 | Ingram ............... C12M 25/00 435/396 |
| 2014/0199679 | A1 * | 7/2014 | Panoskaltsis ......... C12M 25/14 435/2 |

OTHER PUBLICATIONS

Joshua O. Eniwumide, et al., *The development of a bioreactor to perfuse radially-confined hydrogel constructs: Design and characterization of mass transport properties*, Biorheology, 2009.

Kristy M. Ainslie, et al., *Microfabrication of an Asymmetric, Multi-layered Microdevice for Controlled Release of Orally Delivered Therapeutics*, Lab Chip, 2008.

Nasser Sadr, et al., *SAM-based cell transfer to photopatterned hydrogels for microengineering vascular-like structures*, Biomaterials, 2011.

J. Lowry Curley, et al., *Fabrication of Micropatterned Hydrogels for Neural Culture Systems using Dynamic Mask Projection Photolithography*, Journal of Visualized Experiments, 2011.

Excerpt from "2011 Meeting of Medical Fellows and Research Scholars," 2 pages (available Feb. 2011).

Excerpt from "2012 Meeting of Medical Fellows and Research Scholars," 2 pages (available Feb. 2012).

* cited by examiner

MICROFABRICATED POLYMERIC VESSEL MIMETICS

CROSS REFERENCE TO RELATED APPLICATIONS

This application claims the benefit of U.S. Provisional Patent Application Nos. 61/758,198, filed Jan. 29, 2013, and 61/773,064, filed Mar. 5, 2013, which applications are hereby incorporated herein by reference in their entirety.

FIELD OF THE DISCLOSURE

The present disclosure relates to silicone hydrogel and other oxygen transmissive structures, as well as methods of their fabrication and their use in bioreactors and cell cultures.

BACKGROUND

Bioreactors are systems in which biological activity can be sustained. In some cases, bioreactors can be used to stimulate cell growth, chemical reactions, or other activity. Current bioreactors used for cell culture are in need of improvement in various respects to better recapitulate the in vivo environment. As one example, it is often difficult to generate cell clusters greater than several cells in thickness, in part because adequate transportation of nutrients, particularly oxygen, to cells in a cluster becomes more difficult as the distance between the cluster surface and the cells increases.

In some cases, cell viability has been estimated to decrease from about 60% at the cluster surface to about 5% at a distance of 100 μm from the surface. Cells separated from the surface by such a distance can become hypoxic and die, leading to necrosis of the culture. Thus, to more effectively culture cells, it is desirable that nutrients (e.g., oxygen) be made more readily available to, and wastes (e.g., carbon dioxide) be more quickly removed from, the culture volume.

Tissue growth in a living organism requires propagation of blood vessels surrounded by cellular tissue. In some cases, the cellular tissue grows in tandem with the blood vessels, which provides adequate delivery of nutrients to, and efficient removal of wastes from, the cellular tissue. Attempts to mimic such tissue growth in lab-based bioreactors have not been as successful as some have hoped, and in vitro production of biological tissues remains difficult.

Three dimensional (3D) cell culture techniques can provide advantages over two dimensional (2D) cell culture techniques. For example, in the study of biological processes involved in cancer, monolayer cell culture in a 2D environment may not adequately simulate complex features of tumor growth, such as cell morphology, metabolism, migration, signaling, gene expression, and differentiation. Systems that allow 3D culture of cells, for example cancer cells, are desirable because such systems promote more natural cell growth by allowing interactions both between cells and between cells and the extracellular matrix.

Current 3D culture techniques, including explant cultures, 3D scaffolds, and PEG and collagen hydrogels are currently suboptimal. For example, as cultured tumor cells grow into larger structures (i.e., spheroids or clusters) using current 3D culture techniques, the clusters often develop central hypoxia because oxygen is relatively abundant at the culture's surface and less so at its interior. In contrast, tumors in vivo grow around biological vasculature such that hypoxia increases as the distance of the cells from the vasculature increases.

Hydrogels are highly absorbent hydrophilic polymeric materials. Silicone hydrogel materials are biocompatible and have relatively high oxygen permeability. As a result, silicone hydrogels are sometimes used to make contact lenses that provide increased comfort to users and allow users to wear the lenses in the eyes for longer periods of time without inducing corneal hypoxia, edema, or inflammation.

SUMMARY OF THE DISCLOSURE

The present disclosure is directed to embodiments of microstructured oxygen permeable membranes, methods of fabricating microstructured membranes, bioreactors housing microstructured membranes, and methods of using bioreactors and microstructured membranes. In some embodiments, the disclosed devices and material compositions permit culturing of cellular tissues in a 3D culture environment that more accurately resembles in vivo cellular growth conditions. In some embodiments, the membrane surface has an array of microfabricated pillars that mimics a native vasculature system, particularly tissue microvasculature. In one embodiment, this enables the culture of tumor cells in a manner that more closely resembles in vivo tumor cell growth. Bioreactors that incorporate the microstructured membrane as a culture surface also permit improved testing of therapeutic candidate agents. In other embodiments, the present disclosure allows culturing of animal tissues of increased thickness, such as skin tissues leading to improvements in skin and other grafts.

In some embodiments, an oxygen permeable membrane includes a base surface with pillars that project away from the surface, the pillars having a height of greater than about 1 μm and less than about 1 mm to form blood vessel mimetics. In some embodiments, the membrane comprises a silicone hydrogel membrane, the pillars are substantially cylindrical, and the pillars have diameters between about 10 μm and about 100 μm, and heights between about 100 μm and about 500 μm. In some embodiments, the pillars have diameters between about 25 and 100 μm, heights between about 200 and 300 μm, are spaced apart from one another by about 200 μm (measured edge to edge), and have a shear modulus sufficient to withstand stresses induced by fabrication and cell culturing processes.

In some embodiments, the pillars have heights between about 5 and 20 times larger than their diameters, with 7.5 times larger being one example. In some embodiments, the membrane is comprised of a polydimethylsiloxane (PDMS), a methacryloxypropyl terminated polydimethylsiloxane (PDMS), EGDMA (ethylene glycol dimethacrylate), and/or a photoinitiator. In some embodiments, the membrane has a permeability to oxygen that is between about 10 and 100 times that of water.

In some embodiments, the membrane can be housed within a bioreactor comprising an input chamber and an output chamber separated by the membrane that forms a cell culture surface, wherein the input chamber is adapted for connection to a source of oxygen, and the output chamber comprises an oxygen sink with an outlet, such that oxygen from the input chamber flows through the blood vessel mimetics of the membrane into the output chamber. In some embodiments, a cell culture medium having a cellular material therein can be deposited on the membrane in the output chamber. In some embodiments, the cellular material can include human tumor cells, for example, ovarian carcinoma cells.

In some embodiments, a 3-D cell culture bioreactor includes an oxygen permeable membrane comprising a substantially planar surface with pillars that project away from the surface, the pillars having a height of greater than about 1 μm and less than about 1 mm to form blood vessel mimetics, an input chamber, and an output chamber separated from the input chamber by the membrane that forms a cell culture surface, wherein the input chamber is adapted for connection to a source of oxygen, and the output chamber comprises an oxygen sink with an outlet, such that oxygen from the input chamber is capable of flowing through the blood vessel mimetics of the membrane into the output chamber.

In some embodiments, a method of culturing cells in a bioreactor includes providing cells to be cultured and a cell culture medium on the surface of a hydrogel membrane in a bioreactor, and supplying oxygen to the input chamber to perfuse oxygen through the hydrogel membrane into the cell culture medium. In some embodiments, a method of fabricating a hydrogel membrane includes generating a design for a surface of the hydrogel membrane, writing the design onto a photomask, exposing a photoresist material having a thickness of at least about 1 μm to ultraviolet light through the photomask, developing the photoresist material, thereby forming a positive mold in the photoresist material, the positive mold comprising a plurality of pillars having a height of at least about 1 μm, forming a negative mold of the positive mold from a polymeric material, and casting the hydrogel membrane in the negative mold. In some embodiments, the photoresist material is an SU-8 epoxy-based photoresist material, and/or the negative mold is formed from polydimethylsiloxane.

The foregoing and other features and advantages of the invention will become more apparent from the following detailed description of several embodiments which proceeds with reference to the accompanying figures.

DETAILED DESCRIPTION OF SEVERAL EMBODIMENTS

Explanation of Terms

Figure 1:
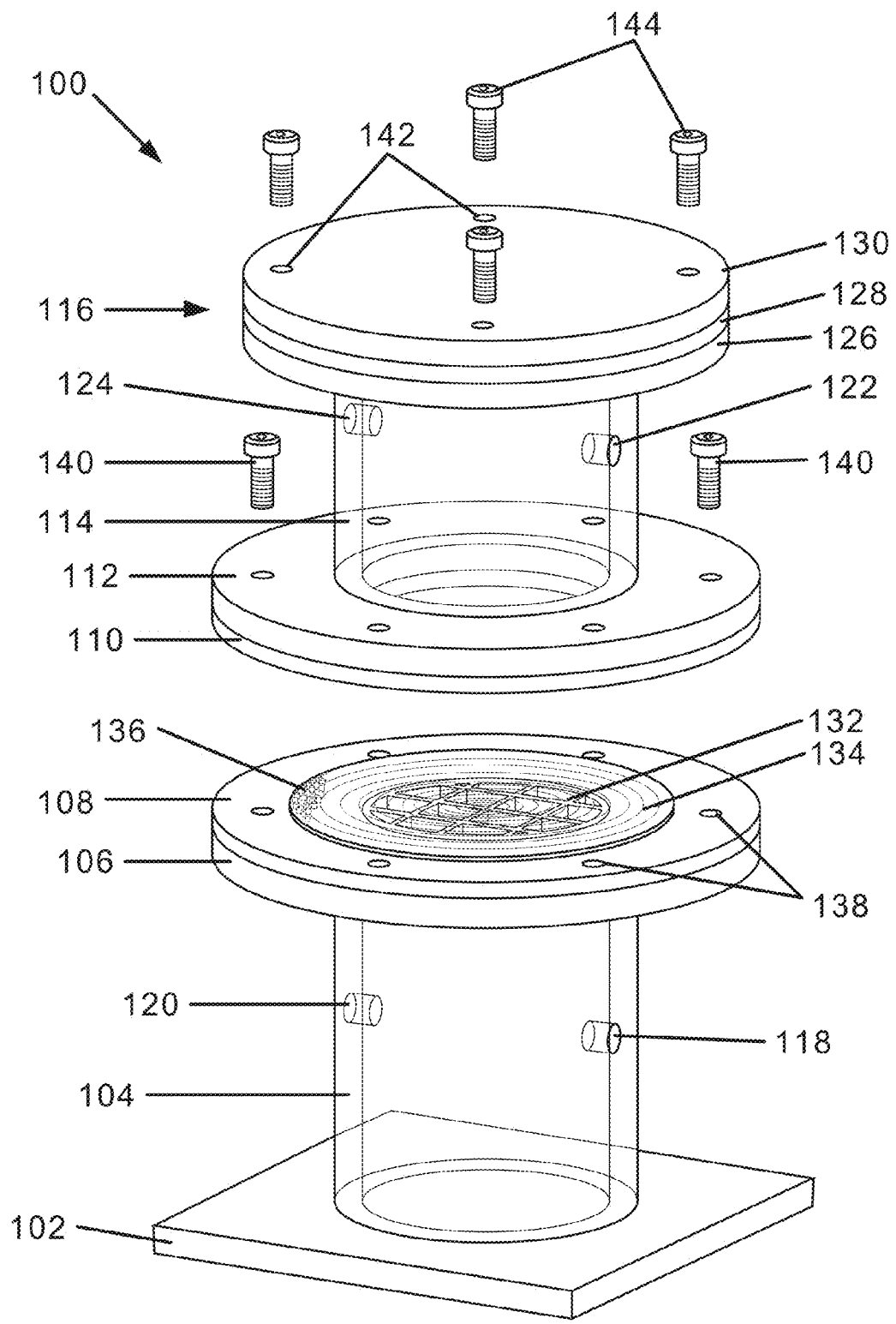
FIG. 1 is a top perspective view, partially expanded, showing an example of one embodiment of a bioreactor.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term unless the context clearly indicates otherwise.

As used herein, "oxygen permeability" can refer to a material property which quantifies the material's ability to deliver oxygen through diffusion. For example, oxygen permeability can be specifically defined as D*k, where D is the diffusivity of the material, and k is the solubility of the material.

Oxygen permeable materials suitable for making the microfabricated arrays disclosed herein can be made of biocompatible materials amenable to microfabrication and having a suitably high oxygen permeability to support cellular growth and sufficient structural permanence to maintain the array in a desired topography. The microfabricated materials are fabricated and not naturally occurring.

A "hydrogel" or "hydrogel material" refers to a polymeric material which can absorb at least 10 percent by weight of water when it is fully hydrated. A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer. "Hydrophilic," as used herein, describes a material or portion thereof that will more readily associate with water than with lipids. "Molecular weight" of a polymeric material (including monomeric or macromeric materials), as used herein, refers to the weight-average molecular weight unless otherwise specifically noted or unless testing conditions indicate otherwise. "Polymer" means a material formed by polymerizing one or more monomers.

Blood vessel mimetics are microfabricated structures that mimic the structure and function of microvessels such as capillaries. In particular embodiments, blood vessel mimetics are pillars on a microfabricated membrane and the blood vessel mimetics can be arranged in an array to mimic physiologic and anatomic features of microvessels, particularly those features relevant to the delivery of oxygen.

A microfabricated array refers to an article having a microscopically visible topography in an ordered or selected arrangement. A microfabricated membrane is a manufactured, non-naturally occurring membrane.

A hydrogel is a hydrated cross-linked polymeric system that contains water in an equilibrium state. A number of hydrogels typically are biocompatible, making them a widely-used material for producing biomedical devices; some hydrogels also have high oxygen permeability. Conventional hydrogels are prepared from monomeric mixtures predominantly containing hydrophilic monomers, such as, 2-hydroxyethyl methacrylate or N-vinyl pyrrolidone. U.S. Pat. Nos. 4,495,313, 4,889,664 and 5,039,459 disclose some conventional hydrogels. Oxygen permeability of these conventional hydrogel materials relates to the water content of the materials, and is typically below 20-30 barriers.

Silicone-containing polymers generally have higher oxygen permeabilities than conventional hydrogels. Silicone hydrogels can be prepared, for example, by curing mixtures containing at least one silicone-containing monomer and at least one hydrophilic monomer. Either the silicone-containing monomer or the hydrophilic monomer may function as a crosslinking agent (a crosslinking agent is a monomer having multiple polymerizable functionalities) or a separate crosslinking agent may be employed. Examples of silicone hydrogels have been disclosed in U.S. Pat. Nos. 4,954,587, 5,010,141, 5,079,319, 5,115,056, 5,260,000, 5,336,797, 5,358,995, 5,387,632, 5,451,617, and 5,486,579, as well as in WO 96/31792.

Polymeric organosilicon compounds are commonly referred to as silicones, and include polymers such as polydimethylsiloxane (PDMS).

Exemplary Embodiments

FIGS. 1-4 show one embodiment of a bioreactor which includes a microstructured membrane with microfabricated pillars formed thereon. FIG. 1 shows a bioreactor 100 including a base plate 102, a cylindrical bottom chamber 104, an annular bottom flange 106, an annular bottom sealing member 108, an annular top sealing member 110, an annular top flange 112, a cylindrical top chamber 114, and a disc-shaped cap 116. The bottom chamber 104 has a first side port 118 and a second side port 120, which allow transmission of gases into or out of the bottom chamber 104. For example, the ports 118, 120 can allow continuous flow of a particular gas or gas mixture through the bottom chamber 104. Similarly, the top chamber 114 has a first side port 122 and a second side port 124 to allow transmission of gases into or out of (e.g., continuous flow of a particular gas or gas mixture through) the top chamber 114. The cap 116 includes a bottom plate 126, an elastomeric sealing plate 128, and a top plate 130. Although not shown, the bottom plate 126 can be annular, allowing the top chamber 114 to extend up to the sealing plate 128.

FIG. 1 also shows a support grid 132 situated between the bottom chamber 104 and the top chamber 114. The support grid 132 is positioned within the central opening formed by annular flange 106 and the annular bottom sealing member 108. The support grid 132 supports a membrane 134 which separates the bottom chamber 104 from the top chamber 114. The membrane 134 is formed from an oxygen permeable material such as PDMS or a silicone hydrogel material that is described in greater detail later. The membrane 134 extends out from the center of the bioreactor 100 such that it can be clamped between the bottom and top sealing members 108, 110, thereby forming an airtight seal between the top and bottom chambers.

On the surface of the substantially planar base of the membrane 134 are formed a plurality of vascular mimetic microfabricated pillars 136. The pillars 136 are shown schematically in FIG. 1 as only partially covering the membrane 134 to enable other features of the bioreactor to be more clearly illustrated, but in practice the pillars 136 cover all of the membrane 134, or any specifically desired portion of the membrane 134. Generally, the pillars 136 can each have a height, diameter, and spacing in the micrometer range (that is, in the range of a few micrometers to hundreds of micrometers). The pillars 136 are drawn at an exaggerated scale in FIGS. 1-3 in order to more clearly illustrate their locations and orientations projecting from a membrane base toward chamber 114.

FIG. 1 shows that the bottom and top cylindrical chambers 104, 114 have similar diameters and are generally aligned with one another. They are sufficiently sealed to the atmosphere such that they can be filled with selected gases that differ from the ambient atmosphere. FIG. 1 also shows that the bottom flange 106, bottom sealing member 108, top sealing member 110, and top flange 112 are generally cylindrical in shape, have similar outside diameters, and are generally aligned with one another. The bottom flange 106, bottom sealing member 108, top sealing member 110, and top flange 112 have a plurality of alignable openings 138 through which fasteners 140, such as bolts or screws, fasten these components to one another. Cap 116 also has a plurality of openings 142 through which a plurality of fasteners 144 are threaded to fasten its components to one another. The sealing members 108, 110, 128 can be, for example, elastomeric components such as soft silicone rubber gaskets.

Thus, FIG. 1 illustrates a bioreactor 100 having two chambers 104, 114, separated by a membrane 134 from which an array of microfabricated pillars 136 project. The ports 118, 120, and 122, 124 of the chambers 104 and 114 allow the gaseous contents of the chambers to be controlled. The bioreactor 100 is preferably airtight and substantially sealed to the atmosphere such that gases can enter or exit the bioreactor 100 only through the ports 118, 120, 122, and 124. In particular, the chambers 104, 114 are airtight such that gases can enter or exit the chambers only through the respective ports or pass between chambers 104, 114 through the membrane 134. Thus, as described in more detail below, a gas, such as oxygen gas (i.e., $O_2$), can flow into the bottom chamber 104, through the membrane 134 into the top chamber 114, and out of the top chamber 114.

In some specific embodiments of the bioreactor 100, oxygen is introduced through ports 118, 120 to create and maintain a fixed concentration of oxygen gas in the bottom chamber 104. Ports 122, 124 create and maintain a lower concentration of oxygen gas in the top chamber 114 than in the bottom chamber 104. In such an embodiment, oxygen tends to diffuse from the bottom chamber 104 (an oxygen source) to the top chamber 114 (an oxygen sink) through the membrane 134. As discussed further below, a cell culture substrate can be supported on an upper surface of the membrane 134. The presence of the pillars 136 facilitates the distribution of oxygen throughout the cell culture substrate supported on the membrane 134 to in turn facilitate cell growth thereon. In some embodiments, a sensor-regulated acrylic hypoxia enclosure (BioSpherix, Ltd., Lacona, N.Y.) can be used for precise, continuous control of oxygen tension in the bottom chamber 104, with the gas concentration in the top chamber 114 controlled by gas flowmeters (Key Instruments, Trevose, Pa.).

Figure 2:
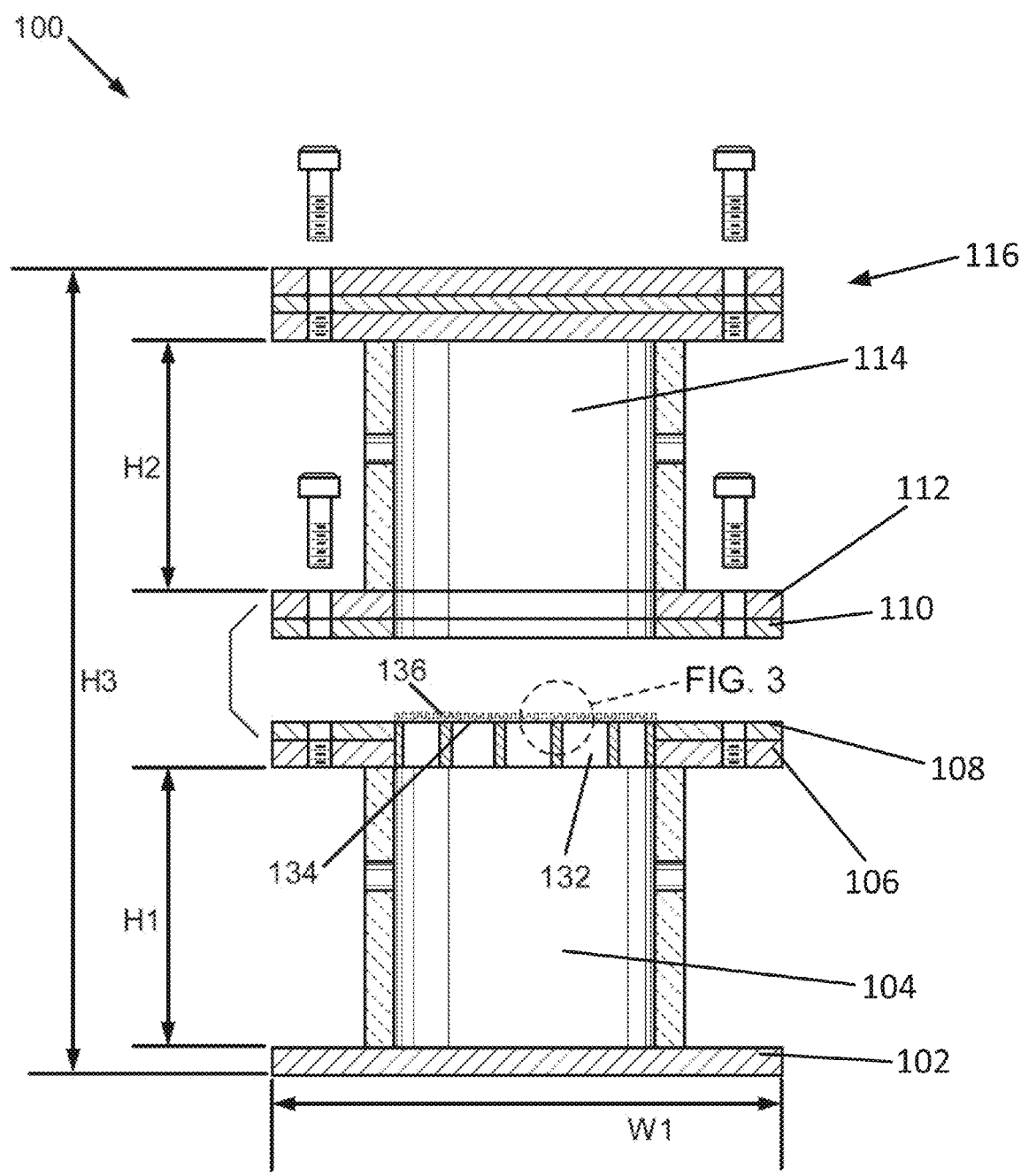
FIG. 2 shows a cross sectional view of the bioreactor of FIG. 1.

FIG. 2 shows the bioreactor 100 in a cross sectional view. The support grid 132, membrane 134, and pillars 136 are positioned within the space created by openings at the center of the annular bottom flange 106, bottom sealing member 108, top sealing member 110, and top flange 112. As shown, the support grid 132 contacts a bottom surface of the membrane 134 to provide mechanical stability and support the weight of the membrane 134 and cell growth medium supported thereon. The membrane can have sufficient strength to locally support the cell growth medium on the grid 132. FIG. 2 also shows that the bottom chamber 104 has a height H1, top chamber 114 has a height H2, the bioreactor 100 has an overall height H3, and the base plate 102 has a width W1.

Figure 3:
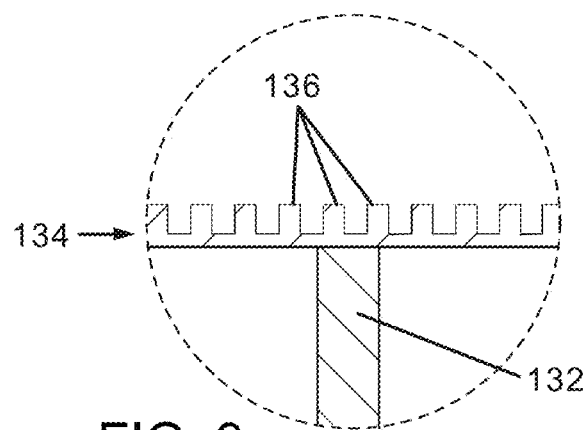
FIG. 3 shows a portion of FIG. 2 at a larger scale, illustrating the oxygen permeable membrane with micropillars that serve as vessel mimetics.
Figure 4:
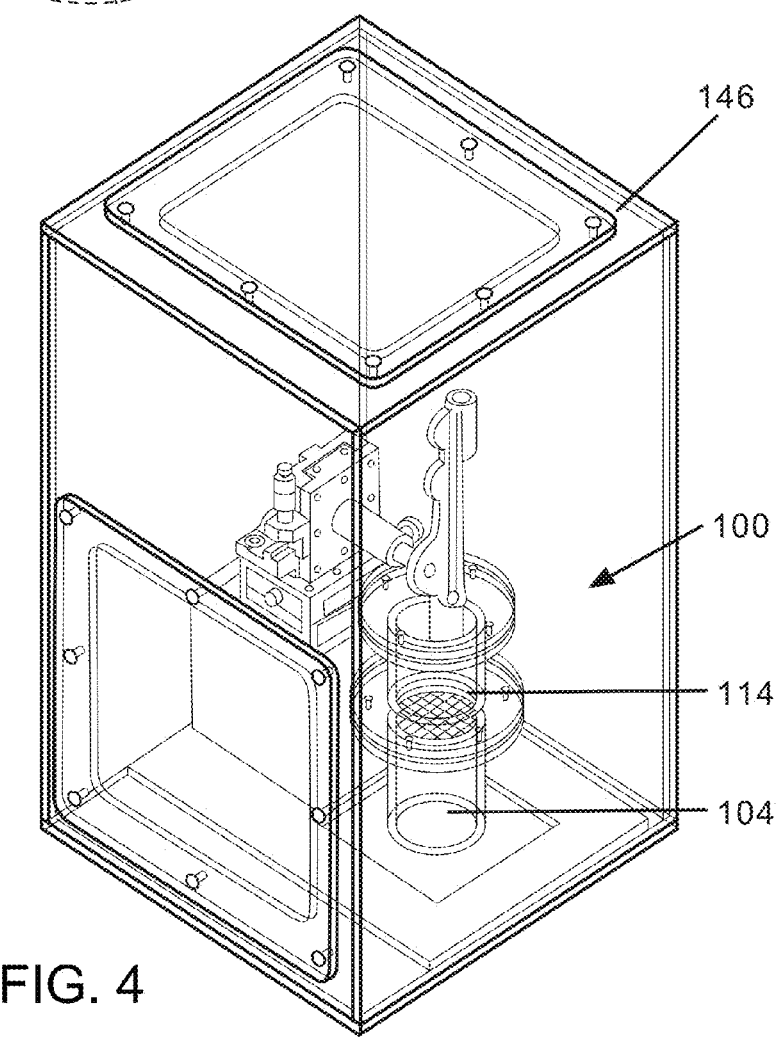
FIG. 4 is a schematic top perspective view of the bioreactor of FIG. 1 housed within an enclosure.

The illustrated base plate 102, bottom flange 106, bottom sealing member 108, top sealing member 110, top flange 112, and cap 116 all have approximately the same diameter, but in alternative embodiments these components can have any appropriate widths and need not have the same width. In one particular embodiment, H1 is about 3 inches, H2 is about 2 inches, H3 is about 6.68 inches, and W1 is about 4 inches. FIG. 3 shows a closer view of the membrane 134 and pillars 136 supported on the support grid 132. FIG. 4 shows the bioreactor 100 in an operational configuration in which an enclosure 146 houses the bioreactor 100 as well as the components necessary to measure and control the gases present in the chambers 104 and 114.

Figure 5:
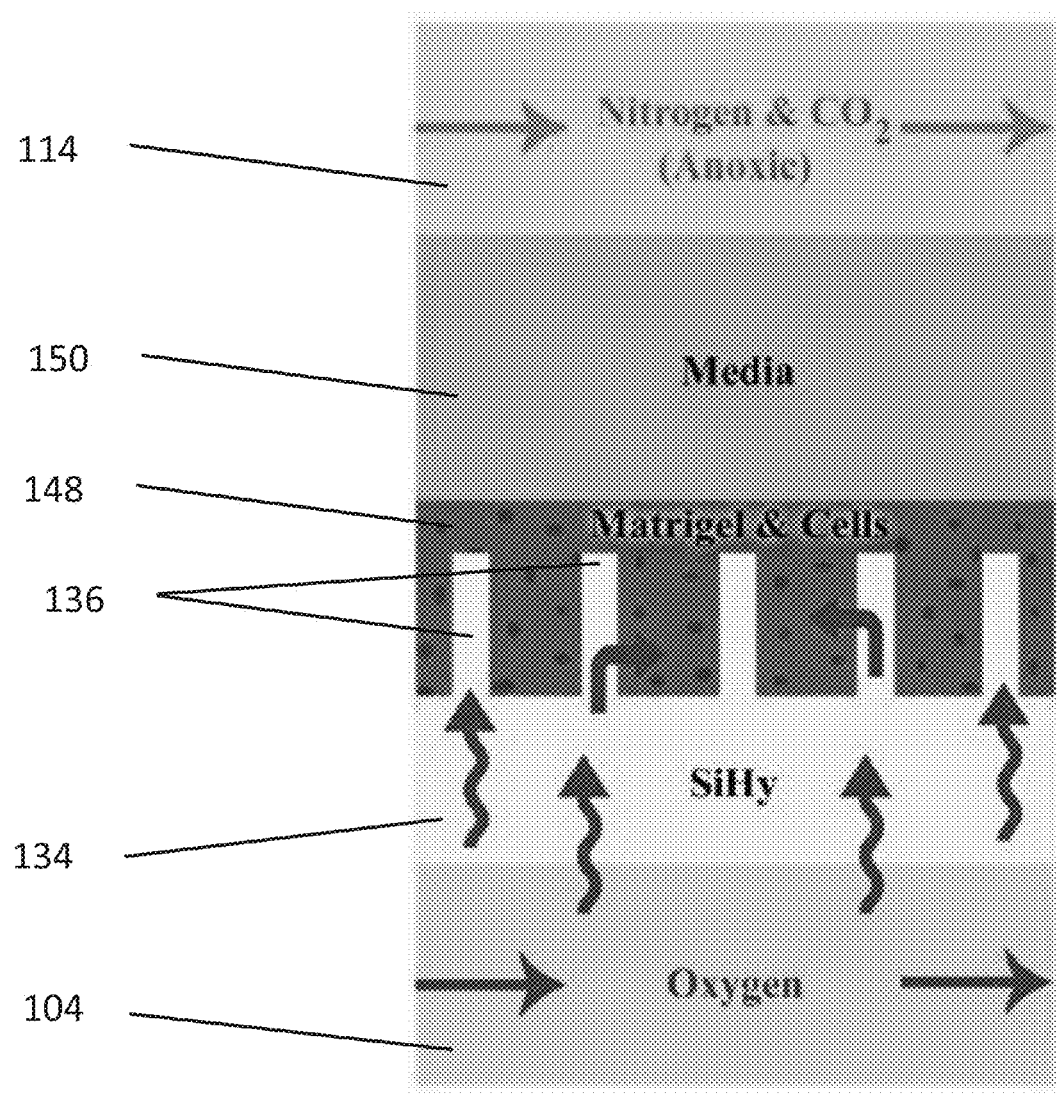
FIG. 5 is a schematic view illustrating oxygen transportation within a bioreactor and a membrane.

FIG. 5 schematically illustrates the oxygen permeable membrane 134 as a silicone hydrogel membrane during operation of the bioreactor 100. As shown, the bottom chamber 104 contains oxygen gas. The top surface of the microstructured membrane 134 in the top chamber 114 is shown covered by a layer of cell culture substrate containing suspended cellular material 148 (described further below), which is covered by a separate layer of a cell growth medium 150 (described further below). The cell culture substrate material and cells are layered on membrane 134 to a depth at least as high as pillars 136. The layer of cell culture substrate can extend above the pillars, for example by an amount comparable to the inter-pillar spacing (i.e., the distance between the centers of adjacent pillars), which is discussed further below. In alternative embodiments, however, the cell culture substrate material and cells need not be layered to a depth at least as high as the pillars.

The top chamber 114 is provided with a relatively low oxygen concentration. Thus, as cultured cells grow in the cell culture substrate 148, around and between the pillars 136, oxygen is provided to the cultured cells by diffusion through the membrane 134 and pillars 136, from the bottom chamber 104 to the top chamber 114. This diffusion is induced at least in part by the oxygen potential created between the two chambers 104 and 114, that is, the difference in the concentration of oxygen between the two chambers 104 and 114. FIGS. 19A-F show the results of finite element modeling of resulting oxygen gradients through the pillars 136 and into the surrounding environment, as further explained below.

Figure 6:
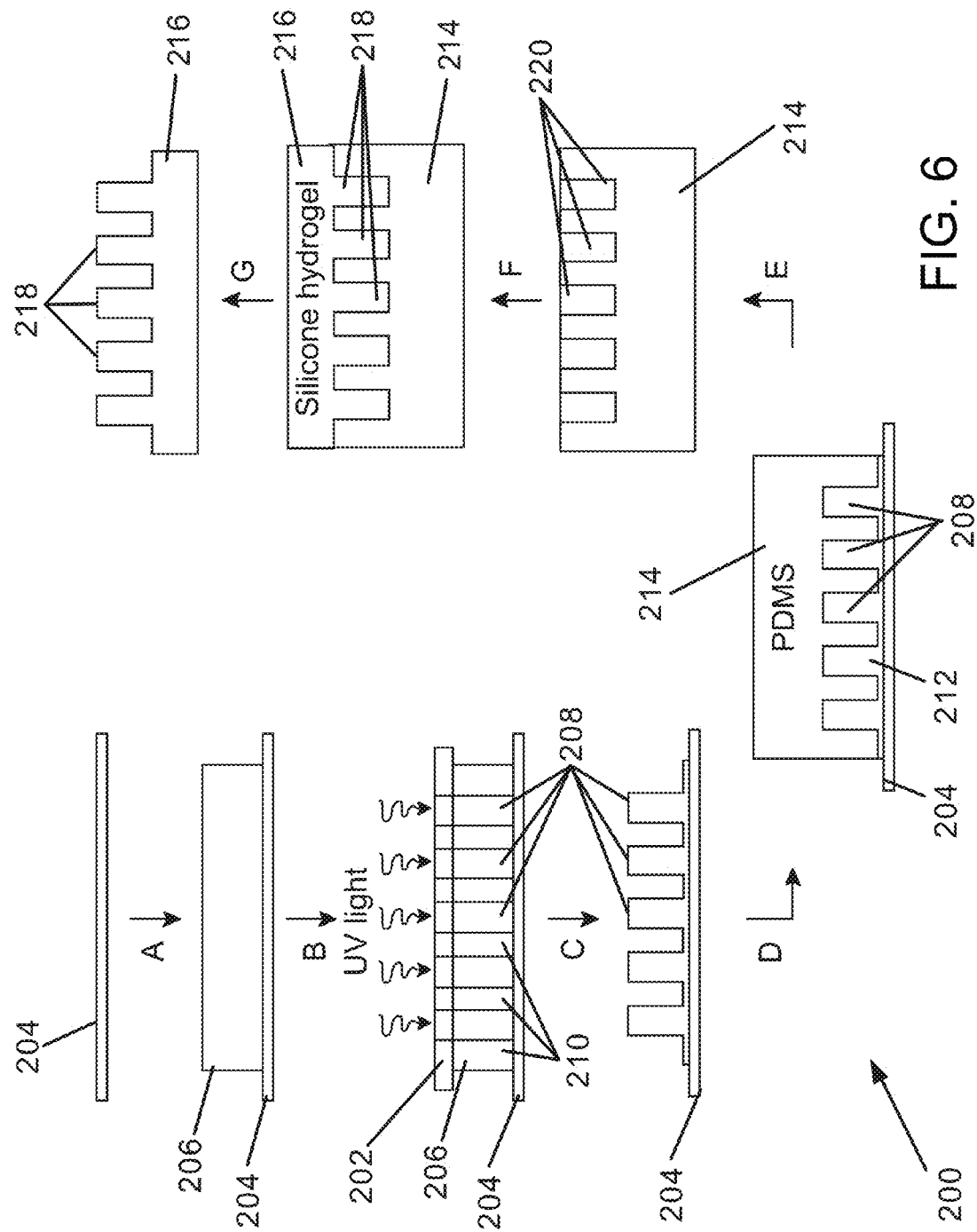
FIG. 6 schematically depicts an example of the process by which a hydrogel membrane having pillars formed thereon can be fabricated.

FIG. 6 shows one exemplary process 200 by which a hydrogel membrane and pillars can be fabricated. The specifically illustrated process 200 uses photolithographic techniques, some of which are known in the art of photolithography. A micropillar design (e.g., patterned circles) is generated using, for example, AutoCAD software, and written onto a photomask 202 using, for example, a DWL66 Laser Writer. FIG. 6 shows that the process 200 continues by providing a silicon wafer substrate 204, which can be baked (e.g., at 200° C. for 20 minutes) and treated with a primer (e.g., MCC Primer 80/20, Marketed by MicroChem Corporation), if needed.

In step A, a layer of high aspect ratio epoxy-based SU-8 photoresist material, such as an SU-2150 photoresist material 206, is formed on the silicone substrate 204, such as by a spin coating process. For example, 1 mL of the photoresist material is deposited onto the substrate per inch of substrate diameter. The substrate and photoresist material is spun to 500 rpm at 100 rpm/s, then at 500 rpm for 10 seconds, then to 2000 rpm at 300 rpm/s, then at 2000 rpm for 37 seconds. The photoresist edge bead is removed from the wafer to improve contact with the photomask and thereby improve resolution and aspect ratio of the final product. The substrate and photoresist material are then put through a soft bake process, baking at 65° C. for 10 minutes, then at 95° C. for 70 minutes.

In step B, the photoresist 206 is exposed to ultraviolet (UV) light through the photomask 202. In some specific embodiments, the exposure of the photoresist layer 206 uses a long pass filter (e.g., a PL-360-LP long pass filter, commercially available from Omega Optical, Inc.) to reduce exposure to radiation below a predetermined wavelength, for example, below a wavelength of 350 nm. Reducing short wavelength radiation helps ensure that the desired structure can be obtained. In some specific embodiments, the photoresist layer 206 is exposed to a plurality of doses of radiation. For example, the photoresist layer 206 can be exposed to two doses of radiation, with the first dose filtered to remove the 350 nm light and the second dose unfiltered, to control the sidewall profile.

In a particular embodiment, the photoresist layer 206 is first exposed to a dose of 713 $mJ/cm^2$ through a long pass filter, then to a dose of 155 $mJ/cm^2$ without a long pass filter. In such an embodiment, the first dose helps ensure the desired structure is obtained, and the second dose can help to ensure adequate crosslinking of the material. After exposure, a post-exposure bake, for example at 65° C. for 5 minutes, then at 95° C. for 25 minutes can be used to catalyze the thermally-driven epoxy cross-linking reaction.

In step C, the exposed photoresist layer 206 is developed using an SU-8 developer as known in the art (commercially available, for example, from MicroChem Corporation) for 20-25 minutes with slight agitation. Development of the photoresist layer 206 causes removal of the unexposed portions 210, but not the exposed portions 208, of the layer 206, due to changed chemical properties of the exposed portions 208. Thus, development of the layer 206 leaves a structure including a one-piece base layer and a plurality of pillars 208 formed from exposed SU-8 material. The surface is then rinsed with isopropanol and hard-baked at 200° C. for 25 minutes. In some cases, a second layer of SU-8 material can be fabricated over this first layer to allow fabrication of membrane structures of greater heights. In some cases, a single, thicker layer of SU-8 can be generated, for example by multiple spin coats or by casting, to allow fabrication of membrane structures of greater heights.

In step D, the developed SU-8 material is silanized, which helps in casting a PDMS mold 214 on the SU-8 structure 212. As one example, tridecafluoro-1,1,2,2-tetrahydrooctyl trichlorosilane is deposited on the SU-8 structure 212 by a 1-2 hour vapor deposition process. A PDMS material is then cast on the SU-8 structure 212. For example, a base and curing agent available in the Sylgard 184 Silicone Elastomer kit made by Dow-Corning can be mixed in a 10:1 ratio by weight, deposited onto the SU-8 structure, and then baked at 80° C. for 90 minutes, thereby forming a PDMS mold 214 on the SU-8 structure 212. In step E, the PDMS mold 214 is then removed from the SU-8 structure 212. In place of the pillars 208, a plurality of wells 220 are left in the PDMS mold 214.

In step F, a silicone hydrogel material 216 is then poured over the PDMS mold 214. The silicone hydrogel material 216 can be composed of any of various appropriate materials, such as 3-methacryloxypropyltris (trimethylsiloxy) silane (TRIS) monomer (commercially available from Silar Labs), methacryloxypropyl terminated PDMS macromer (Commercially available from Gelest, Inc.), N,N'-dimethylacrylamide (DMA) monomer (commercially available from Sigma-Aldrich), N-vinyl-2-pyrrolidone (NVP) monomer (commercially available from Sigma-Aldrich), ethylene glycol dimethacrylate (EGDMA) crosslinking agent, and IRGACURE 2100 UV photoinitiator (commercially available from BASF).

Once poured over the PDMS mold 214, the silicone hydrogel material 216 is exposed to high intensity UV-C radiation having a wavelength in the range of 100-280 nm for 20-25 minutes, which causes photo-polymerization of the hydrogel material 216. The polymerized hydrogel material 216 is allowed to outgas for several hours and is then baked at 80° C. for 10 minutes to facilitate its removal from the PDMS mold 214 by reducing the chance of the pillars 218 shearing under the resulting shear stresses. In step G, the silicone hydrogel material 216 is removed from the PDMS mold 214, thereby forming a hydrogel membrane for use with the bioreactor 100. In order to further reduce the chances that pillars 218 will be sheared off during step G, various solvents, such as toluene or acetone, can be used to cause the PDMS mold to swell, thereby facilitating removal of the hydrogel pillars 218 from the PDMS mold. After removal from the PDMS mold, the silicone hydrogel membrane is washed in acetone and ethanol.

Membranes for use in bioreactors as described herein can be fabricated from various materials. As one specific example, the hydrogel material 216 can include a mixture of 1 mL DMA, 4 mL TRIS, 1 mL methacryloxypropyl terminated PDMS, 0.36 mL NVP, 0.05 mL EGDMA, and 0.051 mL IRGACURE 2100, which are mixed thoroughly by sonication in a Branson 1510 ultrasonic waterbath (such as is commercially available from Emerson Industrial Automation) for 30 seconds three times. As another example, the membrane can be formed from a polyalkoxy siloxane such as polydimethoxylsiloxane (see e.g., U.S. Patent Application Publication Nos. 2008/0085986 and 2013/0178585). As other specific examples, polyethylene glycol (PEG) gels made from crosslinking PEGDA or PEGDMA, or hyaluronic acid gels, in some cases containing silicone components, can be used to form the membrane.

Many other biocompatible, oxygen permeable silicone elastomers can be used to form the membrane. For example, a suitable membrane can be made of a polymeric organo-silicon material having elastic solid properties, such as polydimethylsiloxane (PDMS), or a hydrogel containing PDMS. In some cases, a membrane can be completely fabricated from PDMS (e.g., Dow-Corning Sylgard 184) alone. A membrane including only PDMS can be fabricated according to the method 200, wherein the PDMS mold 214 is silanized (as described above), and another layer of PDMS is poured over the mold 214 to form a membrane having pillars for use in a bioreactor. The PDMS membrane can be cured thermally, as also described above.

The silicone hydrogel composition described above includes DMA, which is hydrophilic and thus serves to make the compound more hydrophilic than PDMS. The relatively hydrophilic compound described above provides some advantages over hydrophobic compounds in protein adsorption which can help improve cell adhesion. Some of the alternative materials described above (e.g., polydimethylsiloxane), however, have been found to provide some benefits in reproducibility of molds and reduced shearing of the pillars during fabrication.

Suitable materials can in various embodiments be biocompatible, sterilizable, amenable to microfabrication, have high oxygen permeability, can be at least temporarily rendered hydrophilic, and/or can be optically clear with relatively low autofluorescence, to enable convenient optical inspection of cell growth in situ. In some cases, the materials described herein as suitable for use as a membrane can have a diffusivity that is about 1.5 to 2 times that of water and can have a solubility of oxygen that is about 8 times that of water.

Figure 7:
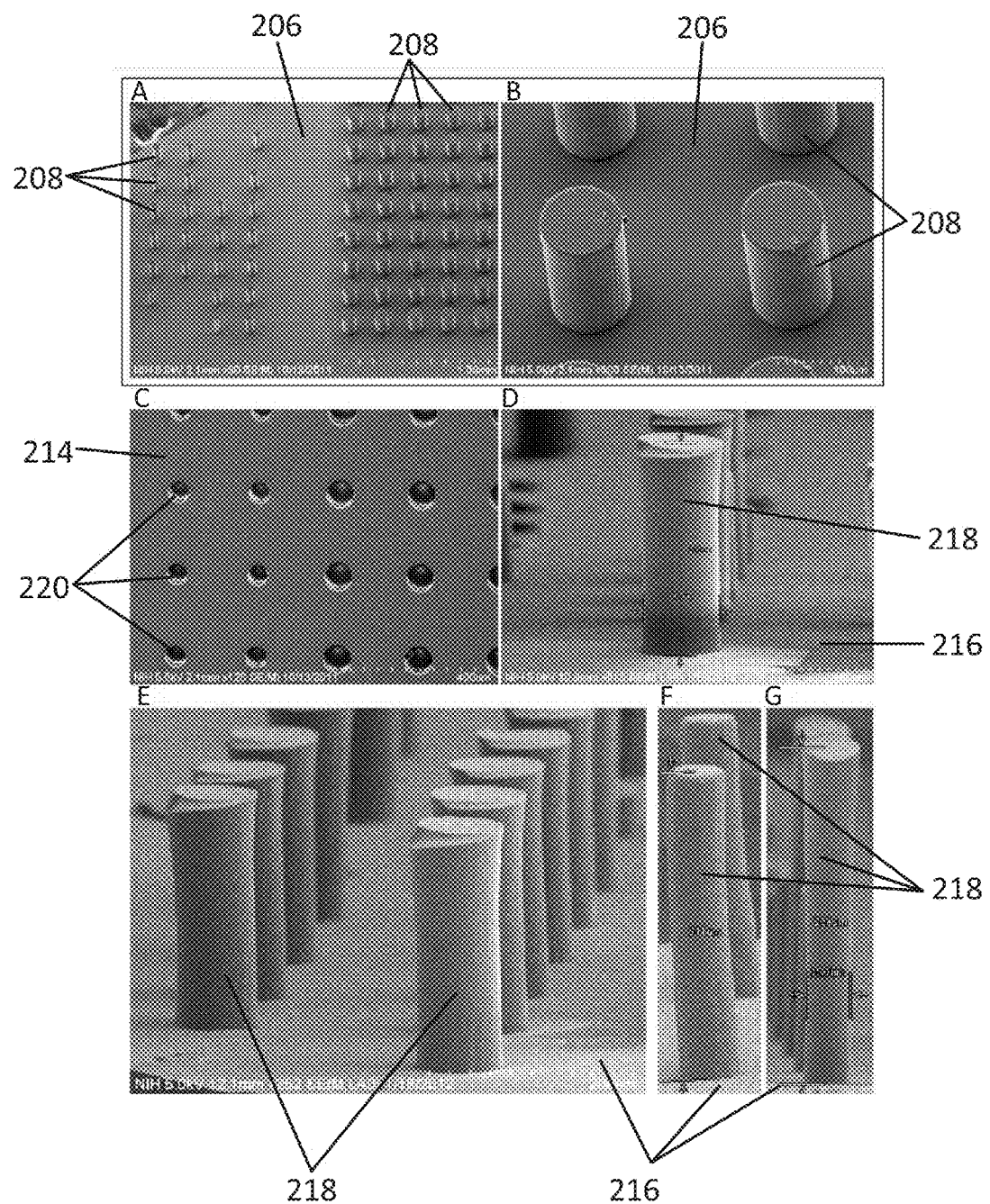
FIGS. 7A and B are photomicrographs that show exemplary photoresist structures formed in the fabrication process of FIG. 6.
FIG. 7C is a photomicrograph that shows an exemplary PDMS mold formed in the fabrication process of FIG. 6.
FIGS. 7D-G are photomicrographs that show exemplary silicone hydrogel membranes formed in the fabrication process of FIG. 6.

FIGS. 7A-G show some of the components described above with regard to process 200. FIGS. 7A-B show that the exposed photoresist layer 206 can have a plurality of pillars 208 arranged in a predetermined pattern such as a plurality of grid like structures, and that the pillars 208 can have various sizes in different embodiments. In the illustrated examples, each membrane has pillars of substantially similar shapes. FIG. 7C shows that the PDMS mold 214 can have a plurality of wells 220 arranged in a grid like structure. In other embodiments, the pillars can be arranged on a hexagonal or any other suitable grid, or set of sub-grids of varying pillar arrangements (e.g., to facilitate multiplex experiments associated with the effects of pillar spacing and corresponding oxygen gradients). FIGS. 7D-G show that the resulting oxygen permeable membrane 216 can include a plurality of pillars 218 with substantially similar or uniform heights, diameters, and profiles. For example, the pillars may be substantially cylindrical as in FIG. 7F, upright, or tilted slightly. The diameter of a pillar can be substantially uniform along its length, or it can have an intermediate, tapered portion. However, the pillars in some embodiments are not tapered from their base on the membrane to their tip, as in a conical or frustoconical shape. Each of the membranes shown can be used in the bioreactor 100, as described above.

It is advantageous that the pillars 218 of the membrane 216 can be fabricated with a relatively high aspect ratio of height to width. Pillars 218 which are significantly taller than they are wide can more accurately reflect the vasculature of native biological tissue. Further, increasing the height of the pillars 218 allows them to pass through several layers of cells in a cell culture. Thus, the pillars 218 fabricated according to process 200 can have a height which is at least about 1 µm. In specific embodiments, the pillars 218 can have diameters between about 1 and 100 µm and heights between about 1 µm and 1 mm. More specifically, pillars can have diameters between about 10 and 100 µm and heights between about 100 and 450 µm, or diameters between about 15 and 100 µm and heights between about 100 and 300 µm or heights between about 200 and 350 µm. Even more specifically, pillars can have diameters between about 25 and 100 µm and heights between about 200 and 275 µm. Even more specifically, pillars can have diameters between about 25 and 100 µm and heights between about 200 and 250 µm.

As one specific example, pillars can have a height of 264 µm and a diameter of 35 µm, and thus an aspect ratio (ratio of height to diameter) of over 7.5. In experiments, aspect ratios of about 20 have been achieved, and the methods described herein can be modified to form pillars with aspect ratios larger than 20. In some cases, pillars having aspect ratios of at least about 2 to about 4 can be particularly advantageous. For example, pillars can have aspect ratios between about 2 and about 10. A nanoliter deposition tool affixed to an xyz positioning table (commercially available from Scienion AG) can be used to deposit materials with focused UV light, allowing the formation of increasingly complex geometries. For pillars that do not have a uniform diameter, an average diameter and an average width may be used to determine the aspect ratio.

In some embodiments, all pillars 218 have substantially the same dimensions. In other embodiments, the pillars 218 need not have the same dimensions and can have differing dimensions (see, e.g., FIG. 7A). While the pillars 218 illustrated in FIGS. 7D-G are all substantially cylindrical in shape, the pillars 218 need not be so shaped. For example, by changing the pattern written onto the photomask in process 200 (i.e., writing geometric shapes other than circles), pillars can be formed with a wide range of shapes, including, for example, squares, ellipses, triangles, and cruciform shapes. The pillars formed through process 200 have been discovered to have a shear modulus sufficient to withstand stresses induced by fabrication and cell culturing processes.

The pillars 218 can be arranged in arrays of pillars 218. As one example, a regular array or matrix of 10,000 pillars arranged in 100 rows of 100 pillars can fit in a total area of 5 mm by 5 mm, or 25 mm$^2$. Thus, a membrane can have a pillar density of around 400 pillars/mm$^2$, for example 300-500 pillars/mm$^2$. In various embodiments, the pillar density can be greater than or less than 400 pillars/mm$^2$. In one embodiment, the pillars can be spaced apart by about 200 µm (measured edge to edge), which allows for the development of a 100 µm oxygen gradient around each pillar, consistent with in vivo capillary density. In other embodiments, the pillars can be spaced closer to or father from one another, for example, the pillars can be spaced by between about 70 and 800 µm. In some cases, a larger pillar spacing can help to facilitate spatial imaging of the effects of oxygen gradient. A single membrane can include a plurality of arrays of pillars 218.

The bioreactor 100, including the membrane 134 fabricated according to process 200, can be used to culture cells. The presence of pillars 136 on the membrane 134 can help to diffuse oxygen through the membrane and to cells cultured thereon, thereby increasing oxygen tension (the partial pressure of oxygen) in the region of cell culture activity. In some cases, a cell culture substrate can be deposited onto the membrane in order to facilitate cell growth thereon. For example, any of various commercially available gelatinous cell growth substrates, such as a BME substrate like Matrigel™, a product commercially available from and marketed by BD Biosciences as a substrate for cell culturing processes, agar, or collagen gels, can be used. Such substrates can allow three dimensional organization of cells and cell-cell contact. Cellular material can be deposited into or onto the cell growth substrate and the membrane for growth thereon. A volume of acellular liquid culture media, for example RPMI 1640 medium (which can be supplemented with fetal bovine serum, penicillin, streptomycin, and/or L-glutamine), loaded on top of the cell-bearing substrate can be used to supply essential nutrients, hydration, and pH buffering.

One result of the cell culture substrate being deposited onto the membrane is that it restricts convective flow of oxygen in the region of the micropillars (e.g., it restricts the rate at which oxygen is carried by water flowing through the substrate), thus limiting oxygen transport primarily to diffusion through the substrate. This can help to mimic in vivo oxygen transport gradients within the substrate in the region of the micropillars. In some cases, the time it takes oxygen to diffuse through the substrate can be equal to or less than the time it takes a convection-driven flow to pass through the substrate. In some embodiments, the time it takes a convection-driven flow to pass through the substrate can be ten times the time it takes oxygen to diffuse through the substrate.

In one specific embodiment schematically illustrated in FIG. 5, cellular material is suspended in a gelatinous substrate such as a Matrigel™ 148, which is then deposited onto the membrane 134 so that the Matrigel™ substantially fills the area between (and optionally over) the pillars. A separate layer of another cell growth medium 150, which can provide nutrients such as sugars and/or amino acids, or buffer the pH of the system, can then be deposited on top of the layer 148. In one specific embodiment, the cellular material is OVCAR8 human ovarian carcinoma cells and the drug resistant sub-line NCI/ADR-Res. In the disclosed examples, these cells are stably transfected with dsRED2 and EGFP, respectively.

Computational Modeling of Bioreactors

Finite element modeling of convective flow and oxygen transport in the bioreactor system was performed using COMSOL. First, a two-dimensional axisymmetric model of the full bioreactor was used to get a reasonable approximation of the convective flow field generated by the thermal gradients that arise from gas delivery and evaporative cooling. This convective flow field was then used together with the measured oxygen source concentration to calculate the development of the oxygen gradient in the bioreactor without cells. Parametric sweeps of the relative oxygen solubility and diffusion coefficient in the silicone hydrogel were used to find best matches for the experimental data on the time-dependent oxygen concentration immediately above the silicone hydrogel surface (described below). The thermal properties of the silicone hydrogel were assumed to mimic acrylic. Other physical constants were obtained from the literature.

With these parameters set, a model with a smaller cell and rectangular symmetry was used in order to be able to include a square array of 50 µm diameter cylindrical pillars in a computationally tractable form. This required the use of an artificially imposed convective field, which was adjusted by choosing vertical flow velocities similar to those found in the full bioreactor calculation and performing parametric sweeps in a 2-D model, with periodic boundary conditions on the edges, to match the oxygen gradient development found in the experimental system and in the full bioreactor computation (described below). Finally, a 3-D model was used that included a square microarray of pillars, using periodic boundary conditions and the 2-D convective flow field found in the earlier calculation with a rectangular cell. Once it was verified that the time-dependent oxygen gradients were essentially unchanged in this 3-D model, the effects of oxygen consumption in the cell-bearing layer were included, based on typical values found in the literature, in order to provide numerical estimates of the steady-state oxygen gradients experienced by the cell clusters.

Using the convective flow velocities from the computational model and the $O_2$ equilibration measurements as a guide, a finite element model was constructed for a square segment of the bioreactor, in order to allow calculation of the detailed $O_2$ concentration around the micropillars. After an artificial convective transport field for this smaller cell was found that produced $O_2$ concentrations matching both the experimental data and the computation for the full bioreactor, the effects of $O_2$ consumption were modeled by assuming uniform cell density in the full Matrigel™ layer. Previously reported models for $O_2$ consumption in close-packed cells were followed, using a Michaelis-Menten form:

$$\text{Rate of } O_2 \text{ consumption} = R_{max} \frac{C_{O_2}}{C_{O_2} + C_{MM}}$$

where $R_{max}$ is the maximum rate of oxygen consumption and $C_{MM}$ is the Michaelis-Menten constant. The Matrigel™ layer was assumed to be uniformly filled with close packed cells and two sets of values found for flask-based culture of EMT6/Ro cells were used, $R_{max}$=0.014 and 0.028 mol/m³-s and $C_{MM}$=2*10⁻³ and 7*10⁻³ mol/m³, respectively. The initial $O_2$ concentration was set to zero everywhere. To simplify the calculation, the source $O_2$ concentration at the top surface of the silicone hydrogel was set to either 32 µM or 84 µM, found by using Henry's law to calculate the concentration of $O_2$ in water in equilibrium with 3% or 8% $O_2$ at 37° C. As a result, these calculations do not include longitudinal concentration gradients along the pillars; from checks made with a single isolated pillar in a 2-D axisymmetric model without oxygen consumption, the $O_2$ concentration at the top of the pillar was estimated to be approximately 10% lower than at the bottom. In addition, it was found that convective flow in the media has minimal effect on the $O_2$ concentration for these consumption parameters, under the simplifying if unrealistic assumption that the Matrigel™ volume is completely filled with cells, and so convective flow was omitted from the calculations that include consumption. Including the convective mixing would become necessary if the actual distribution of cells through a relatively small fraction of the Matrigel™ were taken into account, or if the cellular $O_2$ consumption is lower than assumed here.

Figure 19:
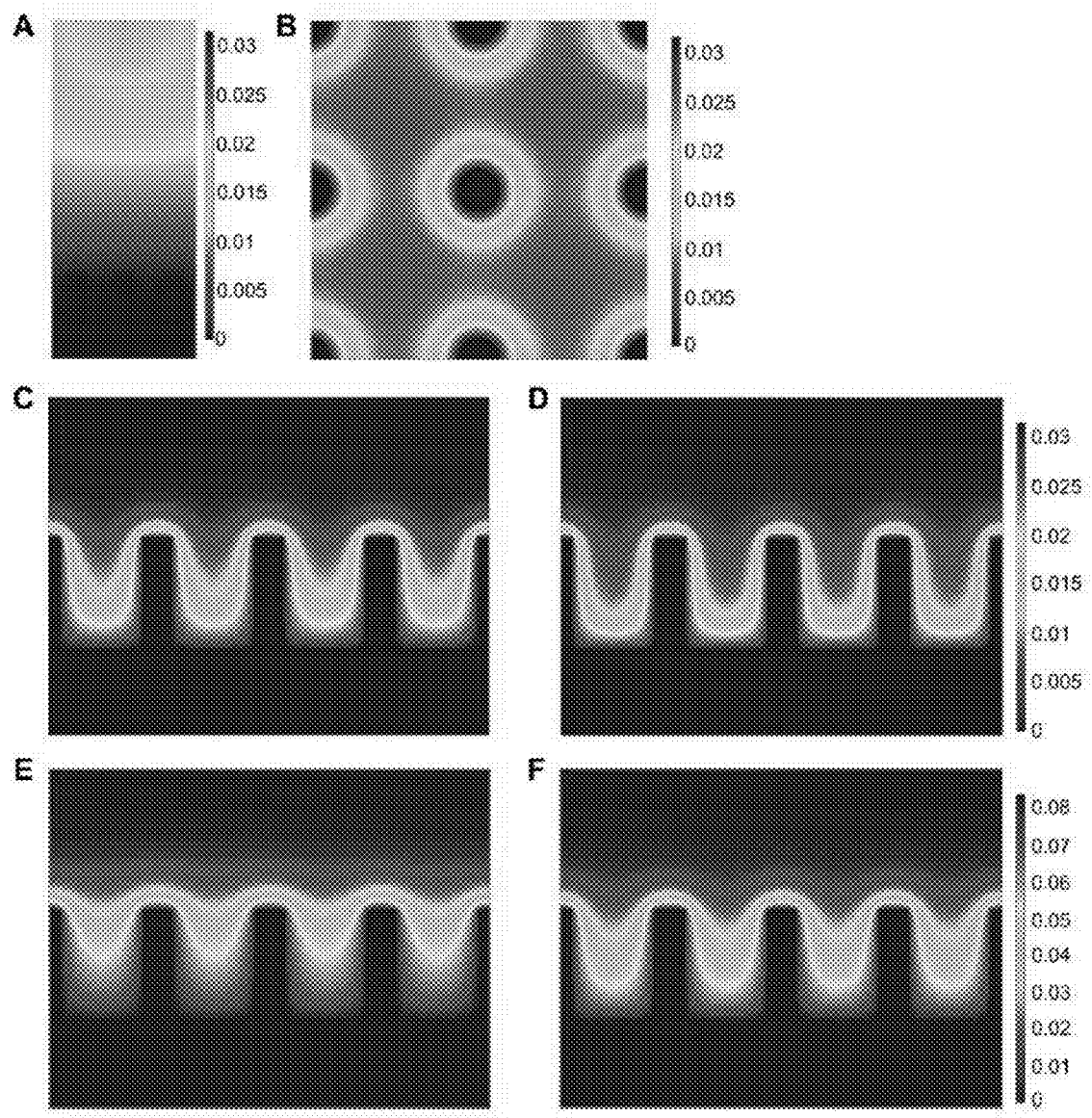
FIGS. 19A-F are images presenting results of 3-D Finite Element Modeling of oxygen gradients around a micropillar array, assuming uniform oxygen concentration in the silicone hydrogel, performed using COMSOL multiphysics software, with the scale bar illustrating mM concentration units.

The results of the 3-D bioreactor calculations are shown in FIG. 19. The equilibrium $O_2$ gradient for a vertical plane transecting the pillars in the absence of cellular $O_2$ consumption, shown in FIG. 19A, is considerably different from that seen with cells present, as shown in FIGS. 19B-F. When $O_2$ consumption is included in the calculations, the $O_2$ concentration falls off sharply away from the pillars, leading to well-defined gradients in the interstitial spaces for all the conditions considered, as shown in FIGS. 19B-E. FIG. 19B shows $O_2$ concentration for a plane horizontally transecting the pillars 100 µm above the SiHy surface, for 3% $O_2$ source concentration and high cellular consumption of oxygen. It was found that the gradients are more pronounced for higher consumption rates, as shown in FIGS. 19D and 19F (where $R_{max}$=0.028 mol/m³-s and $C_{MM}$=7*10⁻³ mol/m³), but still consistent with the observed lateral distribution of cells for the lower consumption rate considered, as shown in FIGS. 19C and 19E (where $R_{max}$=0.014 mol/m³-s and $C_{MM}$=2*10⁻³ mol/m³). Further, the shape of the gradient varies with the source $O_2$ concentration, with a 3% $O_2$ source used for FIGS. 19C and 19D leading to a more rapid decrease away from the pillars than is seen for the 8% $O_2$ source used for FIGS. 19E and 19F, even after rescaling.

Oxygen Diffusion Through a Hydrogel Membrane

To characterize oxygen transport in the bioreactor, and particularly the oxygen permeability of the silicone hydrogel, dissolved oxygen concentration was measured in the bioreactor as a function of distance from a flat silicone hydrogel membrane without cells. For these experiments, the bioreactor was prepared with 0.3% Bacto™ Agar (BD, Franklin Lakes, N.J.), in place of the Matrigel™ used in the cell culture experiments, to a depth of 1 mm above a flat silicone hydrogel membrane, and this agar layer was covered with 15 mm of water, instead of culture media, in order to minimize any biological contamination that might skew the oxygen measurements.

To measure dissolved oxygen tension as a function of distance from the hydrogel membrane, a 500 µm diameter fiber-optic oxygen sensor probe (FOSPOR AL300, SpectrEcology, Jasper, Ga.) was used with the NeoFox™ phase measurement system (OceanOptics, Dunedin, Fla.) and a custom interface written in LabView (National Instruments Corp., Austin, Tex.) to acquire the sensor data. Before taking measurements, both bioreactor chambers were flooded with 100% nitrogen for several hours, until the sensor measured zero oxygen concentration. Upon introduction of 21% oxygen into the bottom bioreactor chamber and continually flowing 95% nitrogen and 5% carbon dioxide through the top chamber, the dissolved oxygen concentration was measured as a function of time at a number of different heights above the silicone hydrogel membrane, with the resulting steady-state values used to extract a gradient profile. The oxygen sensor system was also used for a separate measurement of the time-dependent oxygen concentration in the bottom chamber for use in finite element modeling.

Figure 17:
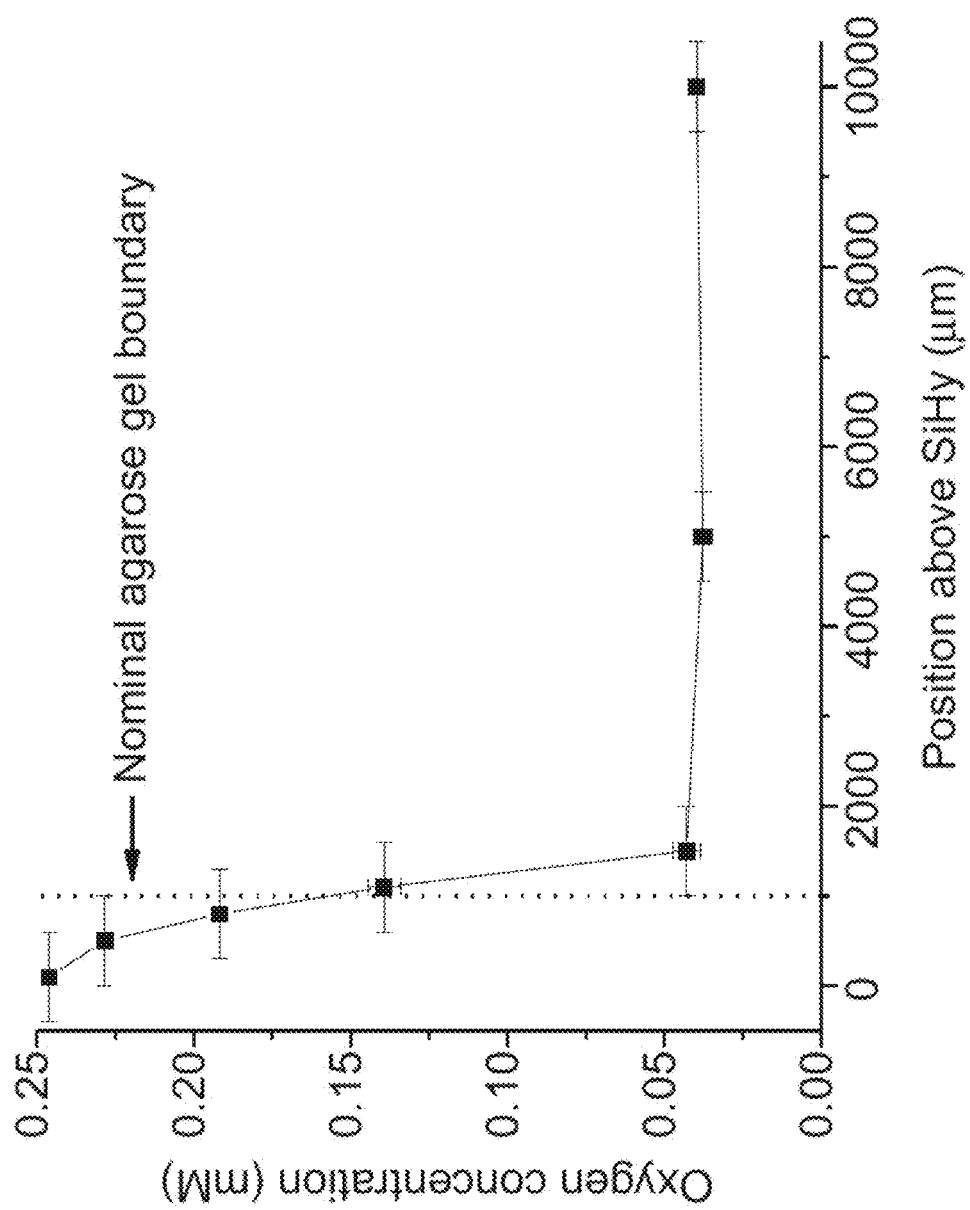
FIG. 17 is a graph showing measured equilibrium oxygen gradient in a bioreactor as a function of distance away from a flat silicone hydrogel membrane, with horizontal bars representing uncertainty and vertical bars representing time-dependent drift in measurements.

From the measurements of oxygen equilibration at different vertical positions in the bioreactor, a steady-state gradient profile was constructed and is shown in FIG. 17. As shown in FIG. 17, the oxygen tension is saturated near the silicone hydrogel surface and falls off sharply in the agar layer where diffusion is the dominant mode of transport. The oxygen concentration in the water above the agar is non-zero and roughly constant as a function of height, likely due to convective mixing in the fluid and limitations in mass transfer across the water-gas boundary at the top surface. It should be noted that in cell culture experiments with gas input of about 8% oxygen, this gradient can encompass a considerably smaller range of concentrations.

Using the COMSOL finite element model of the bioreactor, the expected fluid convection was calculated using input gas temperatures of 34° C. and the external walls of the bioreactor maintained at 37° C. The convective flow was predominantly down in the center of the bioreactor and up at the walls, with maximum velocities on the order of 700 µm/s at the center. Using $3*10^{-9}$ m$^2$/s for the diffusion coefficient of oxygen in water at 37° C. and $7*10^{-6}$ m/s for the oxygen mass transfer coefficient across the interface between the 37° C. water and the anoxic gas, parametric sweeps of the oxygen diffusion coefficient in the silicone hydrogel and the partition coefficient (ratio of oxygen solubilities) between the silicone hydrogel and the agarose were performed. Comparing the results of these sweeps with the experimental data for oxygen equilibration immediately above the silicone hydrogel surface, estimates of the oxygen diffusion coefficient in the silicone hydrogel ($5*10^{-9}$ m$^2$/s), and the partition coefficient (8) were obtained that were in reasonable agreement with numbers found in the literature for similar materials (PDMS).

Figure 18:
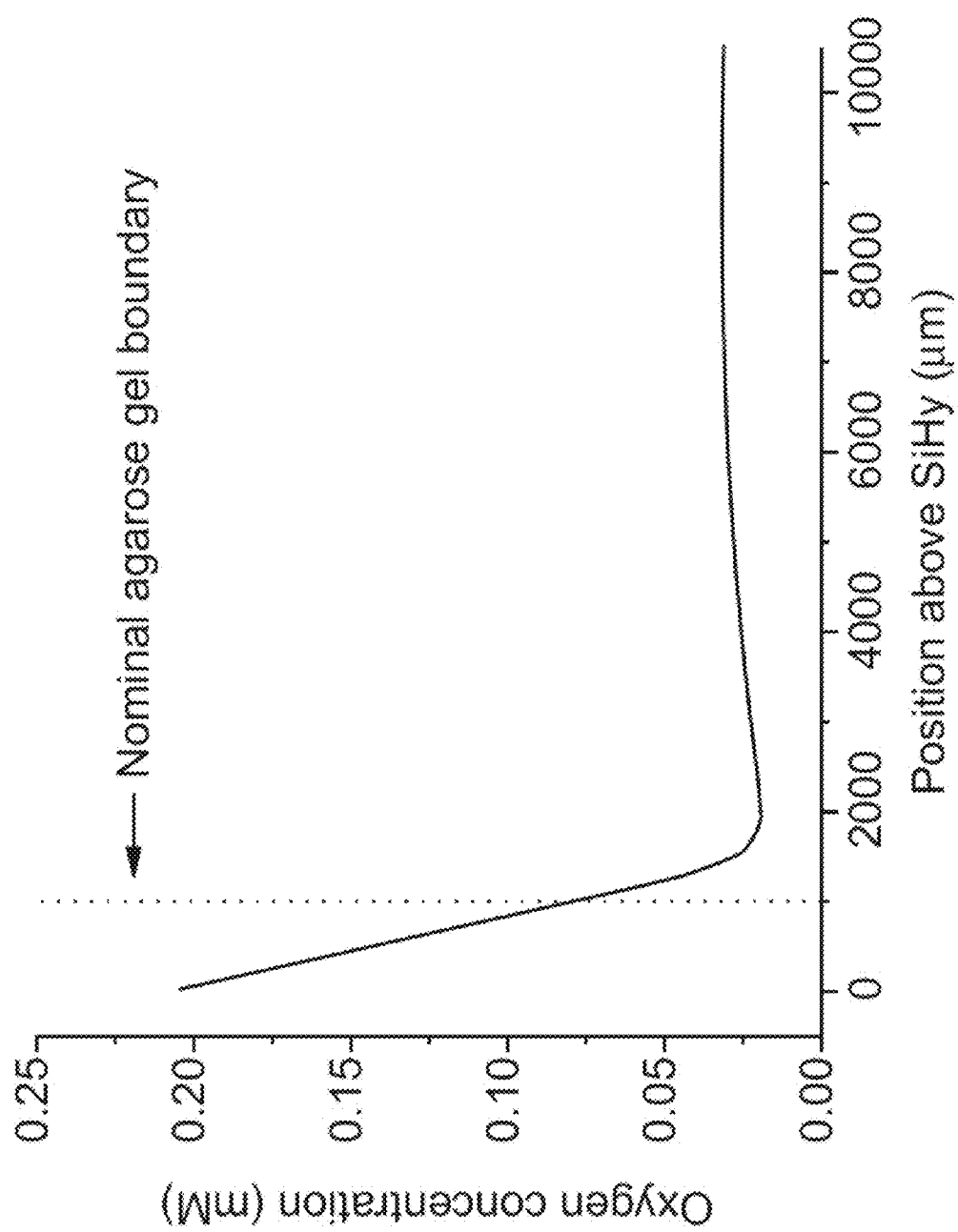
FIG. 18 is a graph showing calculated equilibrium oxygen gradient in a bioreactor as a function of distance away from a flat silicone hydrogel membrane, at the center of a 5 cm diameter cylindrical chamber.

Using these parameters in the finite element model, the steady state oxygen distribution in the full bioreactor was calculated, from which the steady-state oxygen concentration as a position of distance from the membrane was extracted, averaged over a 500 µm diameter area at the center of the bioreactor at each height, as shown in FIG. 18). Given that the simulation essentially has no freely determined parameters, the agreement between the experimental data and the calculation is reasonably good, particularly taking into account known uncertainties in the sensor position. For further verification, the full time-dependent oxygen concentration in the bioreactor was also calculated at heights corresponding to those used in the oxygen measurements, and also found reasonable agreement with the experimental data.

Experimental Results—Cell Growth in a Bioreactor

OVCAR8 human ovarian carcinoma and the drug resistant sub-line NCI/ADR-Res, which were stably transfected with dsRED2 and EGFP, respectively, were used to evaluate the membrane and the bioreactor. Matrigel™ cell growth media was used in the tests. In order to optimize baseline culture characteristics, increasingly concentrated Matrigel™ (1.125, 2.25, 4.5, and 9 mg/mL), having been thawed at 4° C., was seeded with increasingly concentrated cellular material ($1.5*10^5$, $3.0*10^5$, $6.0*10^5$, $1.2*10^6$, $2.4*10^6$, and $4.8*10^6$ cells/mL) in commercial multiwell systems, then imaged using fluorescent microscopy. Optimal cell clusters were seen when the Matrigel™ concentration was between 2.25 and 4.5 mg/mL and particularly at 3 mg/mL, and when the concentration of cells was $6.0*10^5$ cells/mL, although a wide range of cellular concentrations are possible, for example, between $1*10^5$ cells/mL and $5*10^6$ cells/mL.

Matrigel™ control trials were run, in which OVCAR8-dsRed2 cells were embedded in Matrigel™, 250 µL of which (with initial Matrigel™ concentration of 3 mg/mL and initial cellular concentration of $6.0*10^5$ cells/mL) was deposited in each well of untreated 8-well µ-slides (commercially available from Ibidi Gmbh). Each control trial was grown for 7 days at 3% $O_2$, 8% $O_2$ and 21% $O_2$ levels. Gas concentrations referred to herein are measured according to their partial pressures. Diameters of spheroids were quantified using Axiovision software (commercially available from Carl Zeiss Microscopy, LLC). The diameter of a tumor spheroid was defined as the average length of the diameters measured at two-degree intervals passing through the centroid.

Trials were also run in a bioreactor incorporating a silicone hydrogel membrane in accordance with the above description, with pillars having diameters of about 25, 50, or 100 µm, to evaluate the membrane and the bioreactor. Most of the trials were run with pillars having diameters of about 50 µm. 1.8 mL of the Matrigel™ with the OVCAR8-dsRed2 cellular material deposited therein (with initial Matrigel™ concentration of 3 mg/mL and initial cellular concentration of $6.0*10^5$ cells/mL), thus forming 2.0 mL of Matrigel™ and cellular material, combined, was deposited onto the hydrogel membrane in the bioreactor. Thereafter, a layer of 30 mL of RPMI 1640 cell culture medium supplemented with 10% fetal bovine serum (commercially available from HyClone), penicillin, streptomycin, and L-glutamine (commercially available from Invitrogen) was deposited on top of the layer of Matrigel™ and cellular material.

Figure 9:
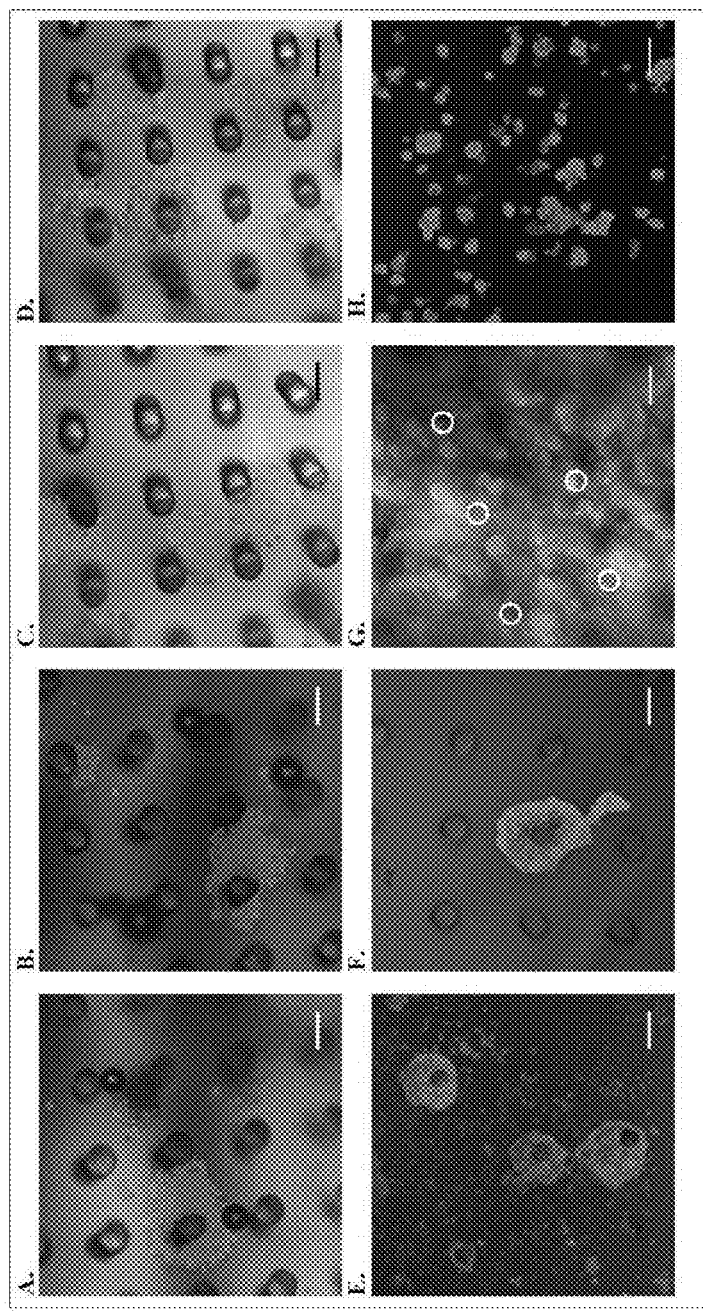
FIGS. 9A-H are a series of photomicrographs depicting cell growth in various environments.

Cells were cultured in the bioreactor in several trials, with the bottom chamber containing, in different trials, 3% and 8% oxygen, which corresponds to 39 and 103 mmHg, respectively, in partial pressure after adjusting for the difference in solubility between $N_2$ and $O_2$ in water. These values can be compared to in vivo arterial blood oxygen which is roughly 75-100 mmHg and venous blood oxygen, which is between 40-50 mmHg. In these trials, the top chamber contained 5% carbon dioxide and the balance was composed of nitrogen gas, except for the control experiment shown in FIG. 9G. FIGS. 9A-G show cells cultured on a hydrogel membrane in a bioreactor in accordance with the above description, in different trials, and as imaged using confocal microscopy. FIG. 9H shows cells cultured in a Matrigel™ control trial (in Ibidi slides) at 8% oxygen for 7 days. Hoechst staining was used and is visible in FIGS. 9E-H.

FIGS. 9A-D show cells cultured in trials in which the bottom chamber was maintained at 8% oxygen and the top chamber was maintained at 95% $N_2$ and 5% $CO_2$ and the cells were cultured for 6 days. FIGS. 9E and F show cells cultured in trials in which the bottom chamber was maintained at 8% oxygen and the top chamber was maintained at 95% $N_2$ and 5% $CO_2$ and the cells were cultured for 7 days. In these two examples, no oxygen is supplied to the top chamber, providing a maximum $pO_2$ differential between the top and bottom chambers. As shown, the cell cultures are clustered around the pillars on the membrane, and display spheroid-like morphology. In addition to forming large multicellular tumor spheroids around the pillars the OVCAR8-dsRed2 cells were able to adhere to the surface of the silicone hydrogel membrane to form a monolayer (best shown in FIG. 9E).

FIG. 9G shows cells cultured in a bioreactor control trial, wherein the top and bottom chambers both contained 3% oxygen and the cells were cultured for 7 days. This trial served as a control, in order to establish that the culture growth in the region of the pillars, exhibited in the trials shown in FIGS. 9A-F, was due to the oxygen gradient established by the different oxygen concentrations in the top and bottom chambers, rather than some other feature, for example, the structural support provided by the pillars. As shown in FIG. 9G, the cultures grown in the absence of the oxygen gradient were relatively evenly distributed across the surface of the membrane, rather than clustered at the pillars, thus resembling the cell growth in the Matrigel™ control trials shown in FIG. 9H, indicating that the oxygen gradient was in fact consequential to the observed growth patterns.

To obtain desired growth patterns, cells can be cultured in a bioreactor having various concentrations of oxygen gas in the bottom and top chambers. The oxygen differential between the bottom and top chambers (i.e., the difference between the concentration of oxygen in the bottom chamber, expressed as a percentage, and the concentration of oxygen in the top chamber, expressed as a percentage) can be at least about 1%, or at least about 2%, or at least about 3%, or at least about 4%, or at least about 5%, or at least about 6%, or at least about 7%, or at least about 8%, or at least about 9%, or at least about 10%, or at least about 12%, or at least about 15%, or at least about 20%, or at least about 21%, or at least about 25%, or at least about 30%, or at least about 35%, or at least about 40%, or at least about 45%, or at least about 50%, or at least about 60%, or at least about 70%, or at least about 80%, or at least about 90%, or about 100%.

In some of the control trials described herein, the differential was about 0%. Some experimental results have indicated that source concentrations ranging from 3% to 8% are particularly desirable, in part because this closely resembles physiological conditions in vasculature, and allows the pillars to more accurately mimic native microvasculature. The oxygen concentration differential should be high enough that significant oxygen gradients are present in the Matrigel™ around the pillars in the top chamber of the bioreactor. If the oxygen concentration is too high, however, then cell growth may be impaired due to oxygen toxicity, and the resulting oxygen gradients around the micropillars may not foster the desired cell growth. In some cases, an optimum or desired oxygen concentration and differential can be based on the diffusivity of oxygen in the particular material used. That is, the oxygen concentrations used in the bioreactor system can be based in part on the material used to obtain desired oxygen concentrations or gradients in the system.

Figure 10:
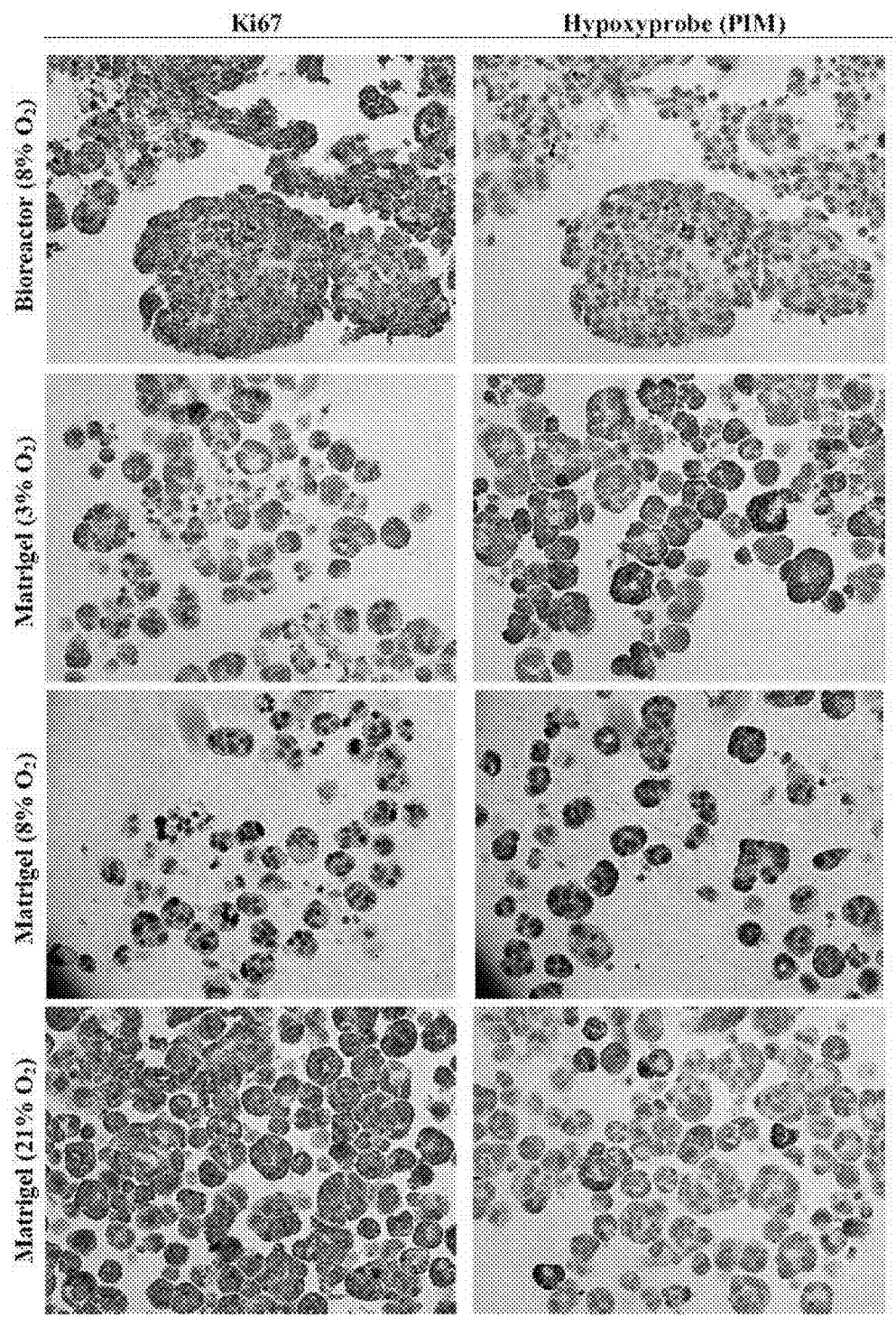
FIG. 10 is a series of photomicrographs depicting cells grown in various environments.

FIG. 10 shows cells cultured in different environments. The first row of images shows OVCAR8-DsRed2 fluorescent cells cultured in a bioreactor as described above, with an oxygen concentration of 8% in the bottom chamber and 0% in the top chamber, for 7 days. The second, third, and fourth rows of images show OVCAR8-DsRed2 fluorescent cells cultured in the Matrigel™ control trials using 250 µL Matrigel™ in the Ibidi µ-slides, at 3%, 8%, and 21% oxygen, respectively, for 7 days. Cell proliferation and hypoxia staining were performed with Ki67 (as shown in the first column of images) and pimonidazole hydrochloride (Hypoxyprobe-1, commercially available from Natural Pharmacia, Inc.) (as shown in the second column of images), respectively.

Cells were incubated for 2 hours in RPMI media containing 200 µM Hypoxyprobe-1 at 37° C. Spheroids collected from the bioreactor and control experiments were fixed in 3.7% paraformaldehyde in PBS for 30 minutes before transferring to PBS. Subsequent paraffin embedding, sectioning and histochemical staining was performed by Histoserve, Inc. Images were taken using a Zeiss Axiovert fluorescence microscope, in brightfield transmission mode. In order to quantify hypoxic gradients within individual spheroids, an image processing script was written in MATLAB (Mathworks, Inc., Natick, Mass.) to spectrally isolate the brown staining and generate a grayscale image. The resultant image was sectioned concentrically and pixel intensities were summed (n=3).

In the Matrigel™ control trial results, illustrated in FIG. 10, increasing oxygen concentration showed a corresponding increase in Ki67 staining, and decrease in pimonidazole staining in 3D Matrigel™ culture, as expected. Little difference was seen in cluster diameters, which were measured between 50 and 70 µm in the Matrigel™ control trials for all oxygen concentrations used. As shown, the bioreactor culture demonstrates a difference in growth morphology compared to 3D culture in Matrigel™ and the results suggest that a lower oxygen tension than 8% is required to achieve hypoxic culture conditions which most accurately reflect those observed in native tissues.

Figure 12:
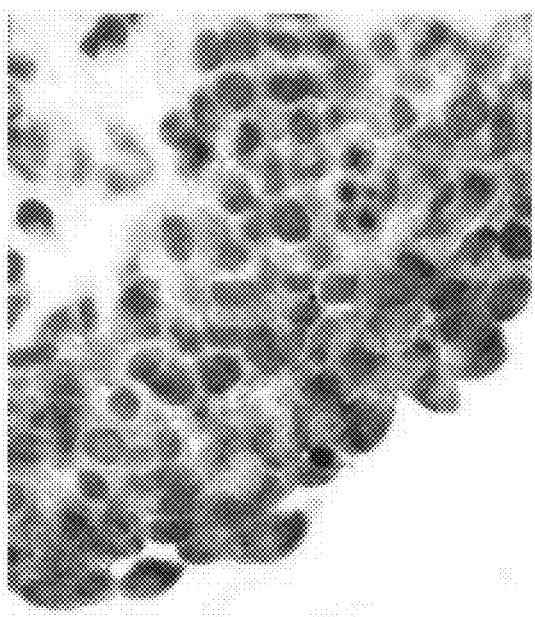
FIGS. 11-12 are photomicrographs depicting a cell cluster extracted from the bioreactor and stained with pimonidazole hydrochloride.
Figure 11:
Figure 13:
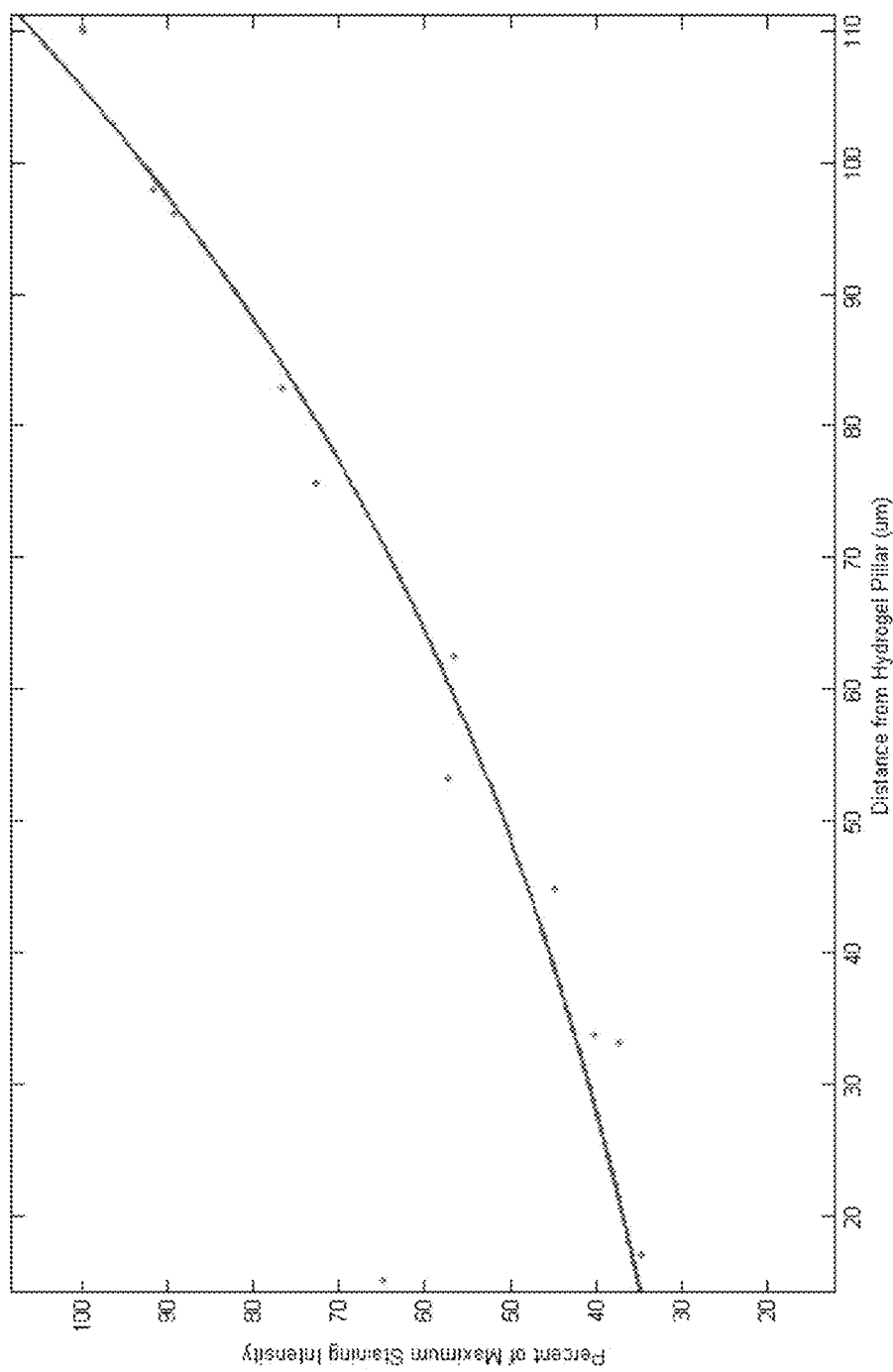
FIG. 13 is a graph showing pimonidazole staining intensity as a function of distance from a hydrogel pillar in the cells of FIGS. 11-12.

FIGS. 11-13 show oxygen gradients present within tumor organoids cultured in a bioreactor system in accordance with the above description. FIG. 11 shows Pimonidazole staining of a tumor organoid (OVCAR8-dsRed2 cells) removed from a silicone hydrogel micropillar (the tumor organoid grew around the micropillar) after a 7 day culture in the bioreactor system, in which the bottom chamber of the bioreactor was maintained at 3% oxygen. The results show increased hypoxia as compared to the hypoxia exhibited in tests run in the bioreactor at 8% oxygen (FIG. 10). FIG. 12 shows a close up view of the image shown in FIG. 11, and shows the gradient in pimonidazole staining intensity used to generate the data presented in FIG. 13, which shows an analysis of staining intensity (hypoxia) as a function of distance from the pillar.

As shown, as the distance from the pillar increases, so does the pimonidazole stain intensity, indicating that hypoxia within a tumor organoid increases with distance from a hydrogel pillar. Notably, this hypoxia gradient is much different from that exhibited by a typical spheroid culture, in which hypoxia increases toward a necrotic, anoxic core of the spheroid. Specifically, the bioreactor results showed that anoxia become especially severe at a distance of about 100 µm from the pillar surface (oxygen source), which is consistent with current understanding of native cell growth.

Figure 14:
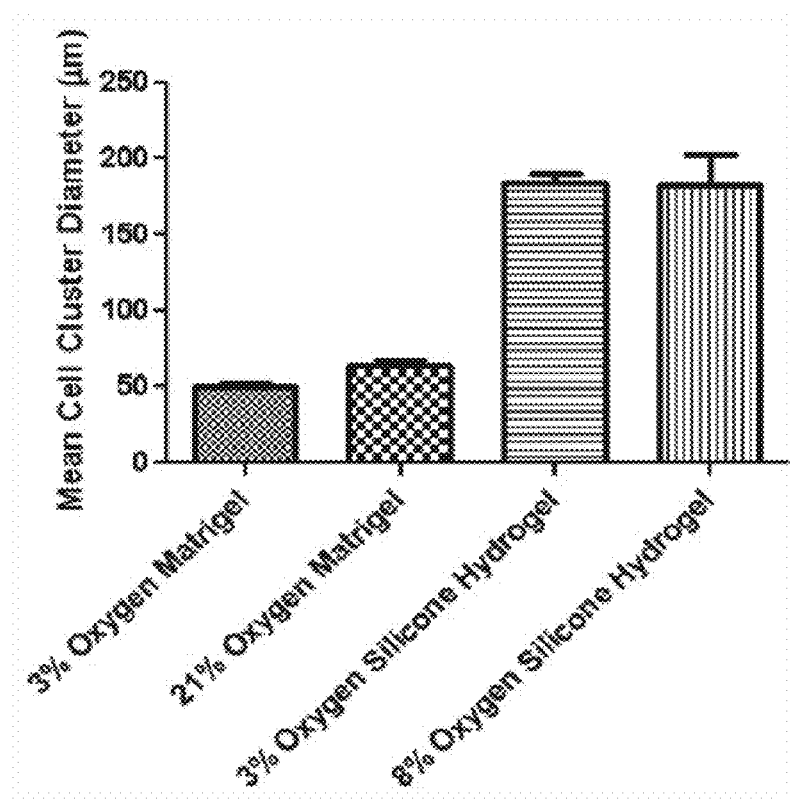
FIG. 14 is a graph showing mean cell cluster diameters in clusters of cells grown in various environments (3% and 21% oxygen in a multiwell plate with Matrigel™; 3% and 8% oxygen source concentration in the bioreactor, with the silicone hydrogel membrane and the cells grown in Matrigel™).

FIG. 14 shows the mean cell cluster diameter of cells cultured for 7 days. The first two bars show the mean cell cluster diameter of cells cultured in the Matrigel™ control trials, while the third and fourth bars show the mean cell cluster diameter of cells cultured in Matrigel™ on a silicone hydrogel membrane with micropillars, as described above. FIG. 14 shows that cell cluster size is greatly increased when cells are cultured using the silicone hydrogel membrane with micropillars. Mean cluster diameter in cultures not using micropillars was about 50 µm, while the mean cluster diameter in cultures which used micropillars was about 183 µm.

Figure 15:
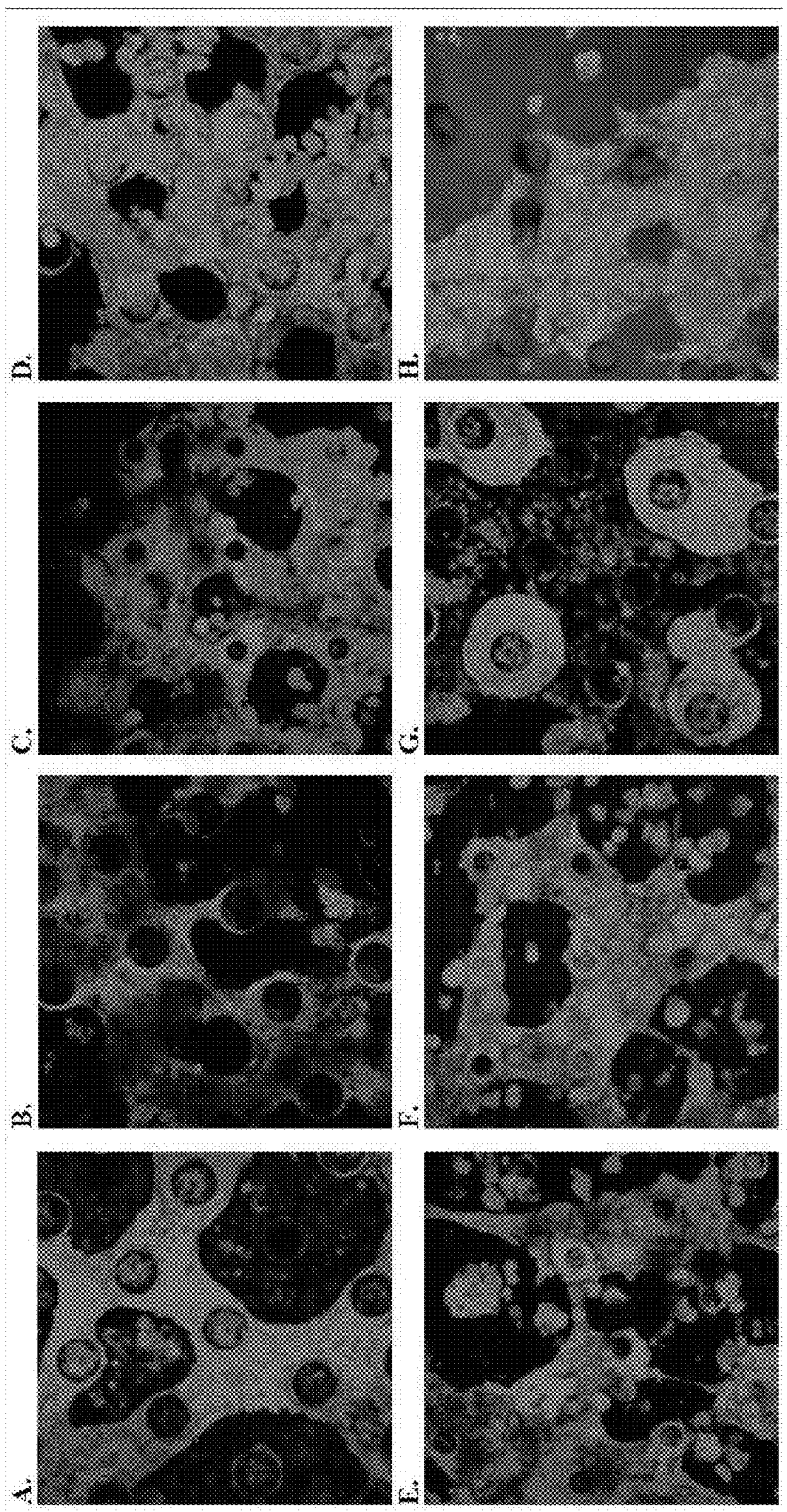
FIGS. 15A-H are photomicrographs depicting maximum intensity projections of confocal z-stack images of OVCAR8-dsRed2 cells with Hoechst stain, cultured in a bioreactor using a PDMS membrane with microfabricated pillars.

FIGS. 15A-H show maximum intensity projections of confocal z-stack images of OVCAR8-dsRed2 cells (red) with Hoechst stain (blue), cultured for 7 days in a bioreactor using an alternative PDMS membrane with microfabricated pillars, with 3% oxygen in the bottom chamber. FIGS. 15A-H show culture geometries similar to those observed with the silicone hydrogel micropillar system described above. PDMS membranes were fabricated by a process similar to that described above for the silicone hydrogel membrane. Branching of cells between the pillars (as shown in FIGS. 15A-F) and clusters around the pillars (as shown in FIG. 15G) were the most commonly observed growth geometries. Notably, cells were seen growing in a monolayer at the surface of the membrane and in larger morphologies at a distance of about 75 µm above the surface of the membrane, possibly suggesting the presence of an optimal oxygen concentration or gradient at that height.

Figure 16:
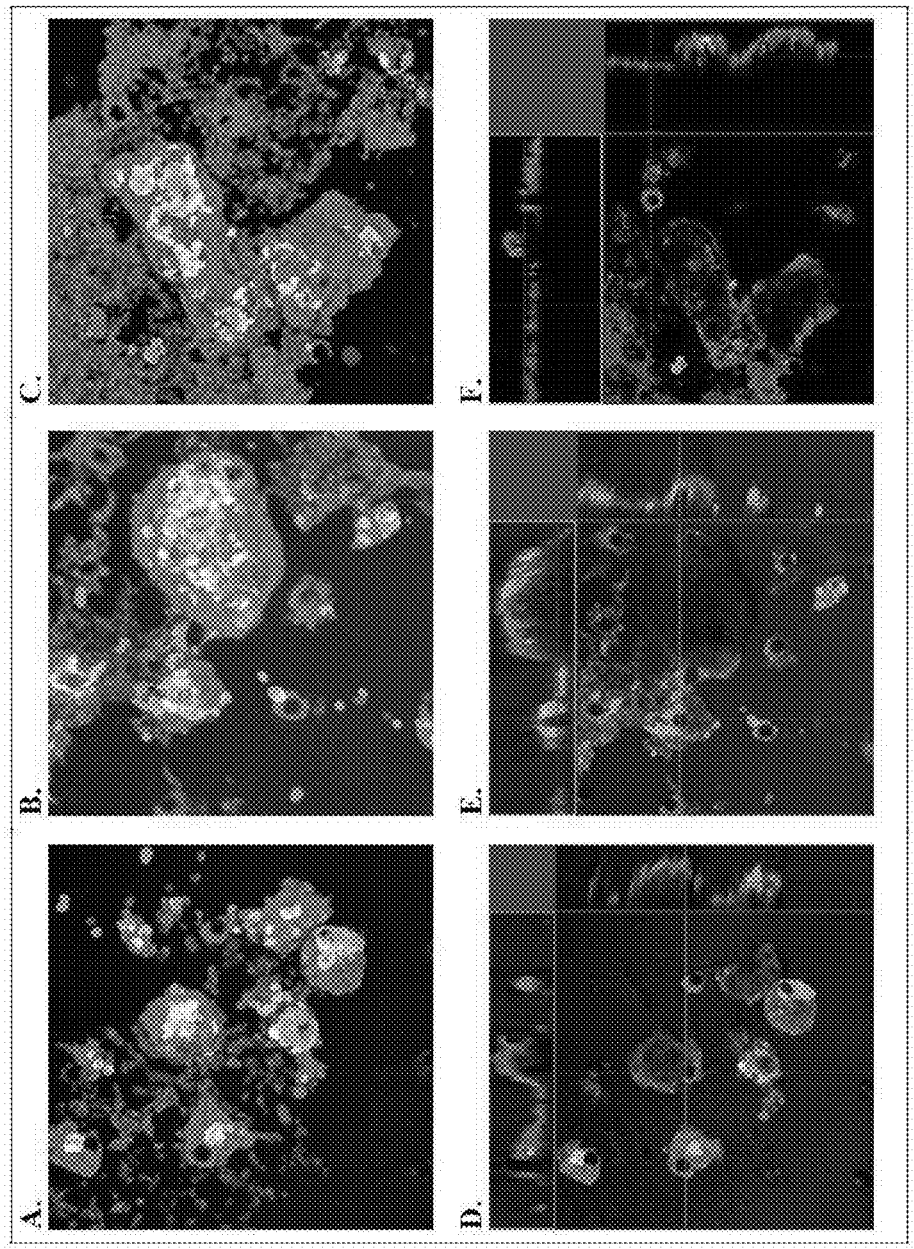
FIGS. 16A-F are photomicrographs depicting OVCAR8-dsRed2 and NCI/ADR-Res EGFP fluorescent cell lines with nuclei stained with Hoechst stain, grown in a bioreactor co-culture trial.

FIGS. 16A-F show OVCAR8-dsRed2 and NCI/ADR-Res EGFP fluorescent cell lines with nuclei stained with Hoechst stain, grown in a bioreactor co-culture trial on a silicone hydrogel membrane. FIGS. 16A-C show maximum intensity projections of confocal z-stack images and FIGS. 16D-F show corresponding views of orthogonal cuts through x, y, and z planes shown at right, top, and bottom left, respectively, of each of FIGS. 16D-F.

Multi-Well Applications

A multi-well insert can be situated on the membrane of a bioreactor so that multiple cell lines can be grown in one bioreactor concurrently, e.g., to help ensure consistent environments for various trials. Such a multi-well insert can also allow culturing of cells in different environments (e.g., different cell growth media) concurrently in a single bioreactor system. Similarly, multiple bottomless culture plates can be situated between two gas chambers, with micropillared membranes in each well, so that multiple cell lines can be grown therein. Similarly, as an alternative to the bioreactor 100, a bioreactor which has multiple vertical openings which connect the bottom chamber to the top chamber, rather than a single such opening, can allow different cell cultures to be grown on separate membranes in each of the openings. In addition to allowing for concurrent culture of multiple samples, such a bioreactor can make fabrication of individual membranes simpler, in part because they need not be as large as a membrane made for the bioreactor 100.

Figure 8:
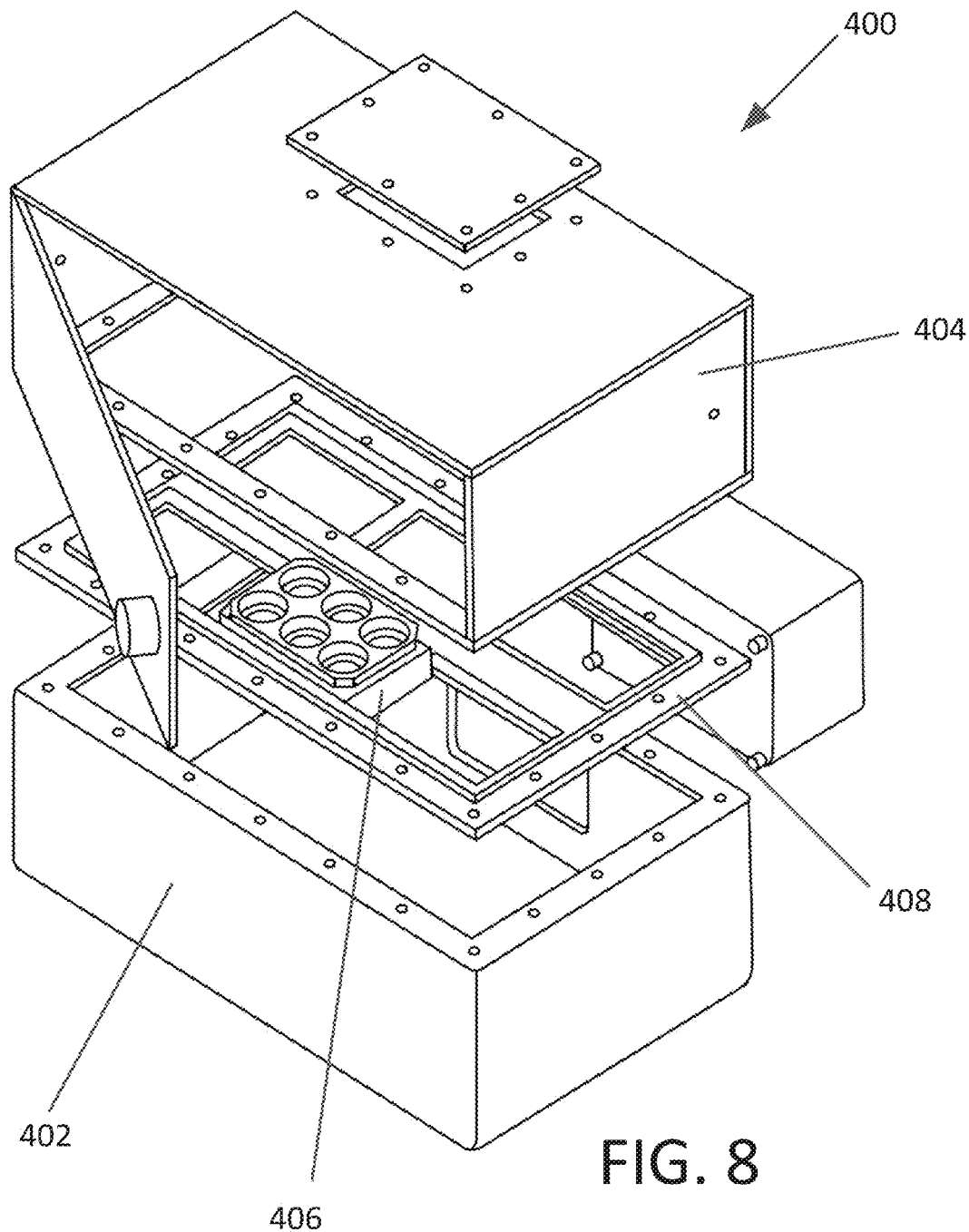
FIG. 8 is a top perspective view, partially expanded, showing an example of one embodiment of a bioreactor with space for up to six multi-well plates.

As one specific example, a 9-well adapter insert can be fabricated from acrylic for cell culture studies, allowing for multiplexed experiments. The 9 wells can allow spatially separated cultures with smaller surface areas, which can help to prevent Matrigel™ detachment from the membrane. As another specific example shown in FIG. 8, a bioreactor 400 can include a bottom input chamber 402, a top output chamber 404, and an intermediate rack 408 for supporting at least one cell culture plate 406. The depicted bioreactor 400 and rack 408 hold up to six multiwell plates 406 to allow for simultaneous testing of multiple pillar geometries and culture conditions thus increasing experimental throughput. In some cases, the multiwell plates can be 6-well plates with the same footprint as a commercial multiwell plate. In some embodiments, plate 406 can include a membrane clamped between an acrylic top element and a stainless steel bottom element held together by screws or magnets. The bioreactor can be configured to enable a user to easily remove culture plates for media exchange and imaging.

Mimetic Improvement

In some cases, it can be advantageous to reduce the diffusion of oxygen from the base surface of the membrane into the cell culture substrate, such that the primary source of oxygen within the substrate is diffusion through the pillars, such that oxygen transport gradients within the substrate in the region of the micropillars more closely resemble in vivo oxygen transport gradients.

As one example, a transferable non-toxic barrier layer can be deposited onto the PDMS mold through a physical means before casting the membrane micropillar array on the mold, such that the barrier layer is transferred to the micropillared structure upon demolding. The physical means can include, for example, evaporative deposition of a weakly adherent metal or semiconductor layer at a high angle (i.e., as measured from perpendicular to the base surface of the membrane), so that minimal material is deposited into the wells, or transferring substantially dry material from a flat surface by stamping, where the material in question could be particles, possibly made of silica, or a polymer layer.

As another example, a barrier layer can be directly deposited onto the micropillar base. This can be achieved, for example, by partially demolding the micropillars, then allowing the thin interstitial space thus revealed to fill with a UV curable prepolymer for an oxygen impermeable material (e.g., polyurethane acrylate (PUA)), for example by capillary action, followed by subsequent curing and full demolding. As another example, a solution of a substantially oxygen impermeable material, or a solution of precursor to an oxygen impermeable material (such as a UV-crosslinkable PUA prepolymer), can be directly deposited on the micropillar array. A combination of forces including gravity and surface interactions can cause the material to cover the base surface of the membrane and prevent the material from coating the pillars. The final height of the layer can be determined by the volume of solution used and the area covered.

As another example, a two-step deposition method can be used, in which the first step is a chemical or physical modification of the flat base area, such that this modification enables subsequent selective deposition of an oxygen-impermeable material, e.g., through charge-based, hydrophilic-hydrophobic, or chemically specific (i.e., covalent linkages) interactions. Such an approach can be particularly advantageous because the relatively impermeable material used in the deposition step does not have to be physically restricted such that it only contacts the base surface.

As another example, the membrane can have a thickness less than or on the order of the pillar spacing, and the bottom surface of the membrane can be laminated with a substantially oxygen impermeable material having holes aligned with the locations of the pillars extending from the top surface of the membrane.

CONCLUSION

The present disclosure provides methods and systems which allow for 3-D culturing of cellular tissues, in part by mimicking native vasculature systems and chemical gradients. 3-D cell cultures can provide various benefits over alternative culturing systems, which can include improved cell morphology, metabolism, migration, signaling, gene expression, and differentiation. The specific structures and methods disclosed herein allow for improved distribution of nutrients, such as oxygen, to a 3-D cell culture through a 3-D membrane structure.

In some specific embodiments, the present disclosure allows culturing of tumor cells on a membrane having a microfabricated pattern which mimics a native vasculature system. This can facilitate the growth and study of increasingly realistic tumors, including modeling and study of tumor angiogenesis, metastasis, and invasion of traditional cell culture. In particular, slowly proliferating tumor cells, such as those seen at greater distances from a blood vessel, are more likely to exhibit drug resistance, particularly towards cell-cycle specific toxins. However, tumor cells grown in artificial cellular environments at conventional $O_2$ tensions are highly proliferative, affecting cell behavior. These differences likely contribute to the discrepancies observed between in vitro- and in vivo-based drug testing. In order to obtain more clinically-relevant data and better predict efficacy of chemotherapeutics, it would be advantageous to mimic oxygenation conditions when developing drug assays and tumor models. Thus, the methods and systems disclosed herein can be used as a drug discovery platform, for example, by incorporating drugs to be tested into the cell growth medium in order to determine its effect on cell growth.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A microfabricated oxygen permeable membrane comprising a base member having a cell culture support surface with solid oxygen-permeable pillars formed thereon that mimic microvasculature in a three-dimensional cell culture, the pillars having respective top surfaces and side surfaces that are oxygen permeable and through which oxygen can diffuse three-dimensionally between and around the pillars, the pillars having a height of greater than 1 µm and less than 1 mm to form blood vessel mimetics that mimic the three-dimensional structure of the microvasculature, the base member and the pillars comprising an oxygen-permeable material, the base member including a bottom surface opposite the cell culture support surface and configured to be exposed to oxygen such that oxygen can diffuse from the bottom surface through the oxygen-permeable material toward the cell culture support surface and three-dimensionally through the pillars toward the top surfaces and side surfaces of the pillars, the base member including a barrier between the pillars that reduces oxygen diffusion through the cell culture surface to preferentially direct oxygen flow diffusing through the membrane into and through the pillars.

2. The membrane of claim 1, wherein the pillars are arranged in a microstructured array.

3. The membrane of claim 2, wherein the pillars are cylindrical and have diameters greater than 10 µm and less than 100 µm, heights greater than 100 µm and less than 500 µm, and are spaced apart by 200 µm.

4. The membrane of claim 3, wherein the pillars have diameters between 25 µm and 100 µm, heights between 200 µm and 350 µm, and a shear modulus sufficient to withstand stresses induced by fabrication and cell culturing processes.

5. The membrane of claim 3, wherein the pillars have heights which are between 2 and 10 times larger than their diameters.

6. The membrane of claim 5, wherein the pillars have heights which are 7.5 times larger than their diameters.

7. The membrane of claim 1 wherein the oxygen-permeable material comprises an organosilicon polymer.

8. The membrane of claim 7 wherein the organosilicon polymer comprises hydrophilicized polydimethylsiloxane (PDMS).

9. The membrane of claim 1 wherein the oxygen-permeable material further comprises:
   (a) a hydrogel;
   (b) an organosilicon polymer;
   (c) a crosslinker and a photoinitiator; or
   (d) some combination of (a), (b), and (c).

10. The membrane of claim 1, further comprising a cell culture bioreactor comprising an input chamber including walls forming a sealed input chamber environment, and an output chamber including walls forming a sealed output chamber environment;
   wherein the membrane is supported on a support grid and separates the input chamber from the output chamber, and wherein the cell culture support surface is hydrophilic;
   wherein the input chamber is adapted for connection to a source of oxygen;
   wherein the output chamber comprises an oxygen sink with an outlet; and
   wherein oxygen from the input chamber is capable of preferentially flowing into and through the pillars into the output chamber as the oxygen diffuses through the membrane to oxygenate a cell culture on the cell culture support surface.

11. The membrane of claim 10, further comprising:
   a culture substrate on the membrane in the output chamber, the cell culture being in the culture substrate; and
   wherein the pillars are covered by the culture substrate such that oxygen can diffuse from the pillars through the cell culture support surface into the culture substrate between and around the pillars.

12. The membrane of claim 11, wherein the cell culture includes isolated human tumor cells.

13. The membrane of claim 12, wherein the tumor cells are ovarian carcinoma cells.

14. The membrane of claim 10, wherein the solid pillars are capable of diffusing oxygen through the solid pillars and between and around the solid pillars in an oxygen gradient that decreases with increasing distance from the solid pillars.

15. The membrane of claim 1, wherein the barrier comprises a substantially oxygen-impermeable material that covers the cell culture support surface but does not cover the pillars to preferentially induce flow of oxygen through the pillars.

16. The membrane of claim 1, wherein the barrier comprises a substantially oxygen-impermeable material having openings aligned with the location of the pillars.

17. The membrane of claim 16, wherein a thickness of the base member is less than or equal to an inter-pillar spacing.

18. The membrane of claim 1, wherein the pillars are solid pillars consisting of a silicone hydrogel.

19. The membrane of claim 1, wherein the pillars are solid pillars consisting of polydimethylsiloxane.

20. The membrane of claim 1, wherein the cell culture support surface is hydrophilic to increase adherence of the cell culture on the top and side surfaces of the pillars.

21. The membrane of claim 1, wherein oxygen can diffuse from central regions of the solid pillars through the side surfaces and the top surfaces of the pillars without reacting with the pillars.

22. The membrane of claim 1, wherein the solid oxygen permeable pillars are hydrophilic hydrogel pillars.

23. The membrane of claim 22, wherein the solid oxygen permeable pillars comprise 3-methacryloxypropyltris(trimethylsiloxy)silane (TRIS), methacryloxypropyl terminated polydimethylsiloxane, N,N'-dimethylacrylamide (DMA), N-vinyl-2-pyrrolidone (NVP), or ethylene glycol dimethacrylate (EGDMA).

24. The membrane of claim 1, further comprising a cell culture bioreactor.

25. A cell culture bioreactor comprising:
   the microfabricated oxygen permeable membrane of claim 1 that forms blood vessel mimetics;
   an input chamber; and
   an output chamber separated from the input chamber by the membrane such that the base surface forms a cell culture surface;
   wherein the input chamber is adapted for connection to a source of oxygen;
   wherein the output chamber comprises an oxygen sink with an outlet; and
   wherein oxygen from the input chamber is capable of flowing preferentially through the pillars into the output chamber to oxygenate the cell culture.

26. The bioreactor of claim 25, further comprising:
   a culture substrate on the membrane in the output chamber; and
   a cellular material in the culture substrate.

27. The bioreactor of claim 26, wherein the cellular material includes human tumor cells.

28. The bioreactor of claim 25, wherein the microfabricated membrane comprises an organosilicon polymer.

29. A method of culturing cells in the bioreactor of claim 10, comprising:
   providing cells to be cultured in a culture substrate on the base surface of the microfabricated oxygen permeable membrane; and
   maintaining an oxygen gradient between a second surface of the membrane and a surface of the culture substrate separated from the base surface of the membrane to perfuse oxygen through the pillars into the culture substrate.

30. The method of claim 29, wherein the cellular material comprises tumor cells.

31. The method of claim 29, wherein the microfabricated membrane comprises an organosilicon polymer.

32. A microfabricated oxygen permeable membrane comprising an oxygen-permeable material, the membrane having a hydrophilic cell culture support surface forming an array of solid oxygen permeable pillars that mimic microvasculature in a three-dimensional cell culture, the membrane having a bottom surface opposite the cell culture support surface and configured to be exposed to oxygen such that oxygen can diffuse through the oxygen-permeable material from the bottom surface toward the cell culture support surface, and three-dimensionally through the pillars toward respective top surfaces and side surfaces of the pillars, the pillars having a height of greater than 1 μm and less than 1 mm that mimic the three-dimensional structure of the microvasculature.

33. The membrane of claim 32, wherein the solid pillars consist of the oxygen-permeable material.

\* \* \* \* \*